United States Patent
Kaplan et al.

(10) Patent No.: US 8,859,752 B2
(45) Date of Patent: Oct. 14, 2014

(54) SIRNA-BASED THERAPY OF FIBRODYPLASIA OSSIFICANS PROGRESSIVA (FOP)

(71) Applicant: The Trustees of the University of Pennsylvania, Philadelphia, PA (US)

(72) Inventors: Frederick S. Kaplan, Philidelphia, PA (US); Eileen M. Shore, Fort Washington, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 13/654,208

(22) Filed: Oct. 17, 2012

(65) Prior Publication Data

US 2013/0041017 A1     Feb. 14, 2013

Related U.S. Application Data

(63) Continuation-in-part of application No. 12/296,275, filed as application No. PCT/US2007/009357 on Apr. 17, 2007.

(60) Provisional application No. 60/792,646, filed on Apr. 18, 2006.

(51) Int. Cl.
  *C12N 15/11* (2006.01)
  *C07H 21/04* (2006.01)
  *A61K 31/713* (2006.01)
  *C12N 15/113* (2010.01)

(52) U.S. Cl.
  CPC ............ *A61K 31/713* (2013.01); *C12N 2310/14* (2013.01); *C12N 2320/34* (2013.01); *C12N 15/1138* (2013.01)
  USPC ........................................ 536/24.5; 514/44 A

(58) Field of Classification Search
  USPC ........................................ 536/24.5; 514/44 A
  See application file for complete search history.

(56) References Cited

U.S. PATENT DOCUMENTS

| | | |
|---|---|---|
| 5,863,738 A | 1/1999 | Dijke et al. |
| 5,925,517 A | 7/1999 | Tyagi et al. |
| 6,028,290 A | 2/2000 | Yasuhara et al. |
| 6,060,240 A | 5/2000 | Kamb et al. |
| 6,150,107 A | 11/2000 | Glazer et al. |
| 6,297,016 B1 | 10/2001 | Egholm et al. |
| 6,316,230 B1 | 11/2001 | Egholm et al. |
| 6,316,610 B2 | 11/2001 | Lee et al. |
| 6,709,813 B1 | 3/2004 | Bergmeyer et al. |
| 2004/0058334 A1 | 3/2004 | Kaplan et al. |

OTHER PUBLICATIONS

Wharam et al., "Specific detection of DNA and RNA targets using a novel isothermal nucleic acid amplication assay based on the formation of a three-way hunction structure" Nucleic Acids Res. Jun. 1, 2001;29(11):E54-E54.

Aldea et al. "Rapid Detection of Herpes Simplex Virus DNA in Genital Ulcers by Real-Time PCR Using SYBR Green I Dye as the Detection Signal" J. Clin. Microbiol. 40:1060-1062 (2002).

Feldman et al., "Ficrodysplasia Ossificans Progressiva, a heritable disorder of severe heterotopic ossification, maps to human chromosome 4q27-31", Am. J. Hum. Genet. 66:128-135, 2000.

Tan et al., "Molecular Beacons", Current Opinion in Chemical Biology 2004, 8:547-553.

*Primary Examiner* — Jon E Angell
(74) *Attorney, Agent, or Firm* — Mark S. Cohen; Pearl Cohen Zedek Latzer Baratz LLP

(57) ABSTRACT

This invention is directed to mutated Activin A type I receptor proteins (ACVR1) and isolated nucleic acids encoding same. The invention also relates to compositions and methods for siRNA-based regulation of mutated ACVR1 expression in the treatment of Fibrodysplasia Ossificans Progressiva (FOP).

9 Claims, 10 Drawing Sheets

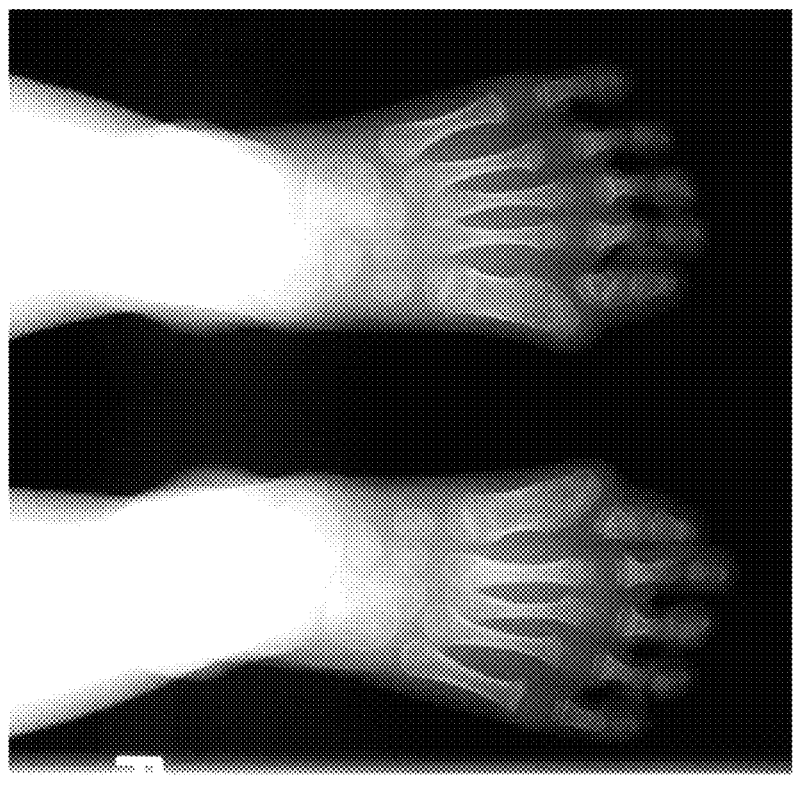
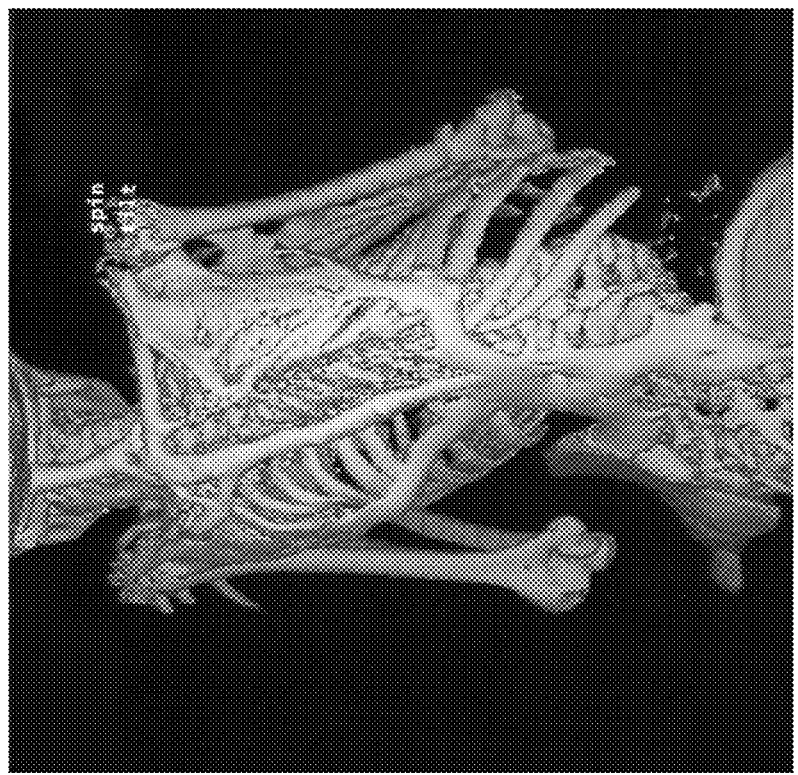
Figure 1

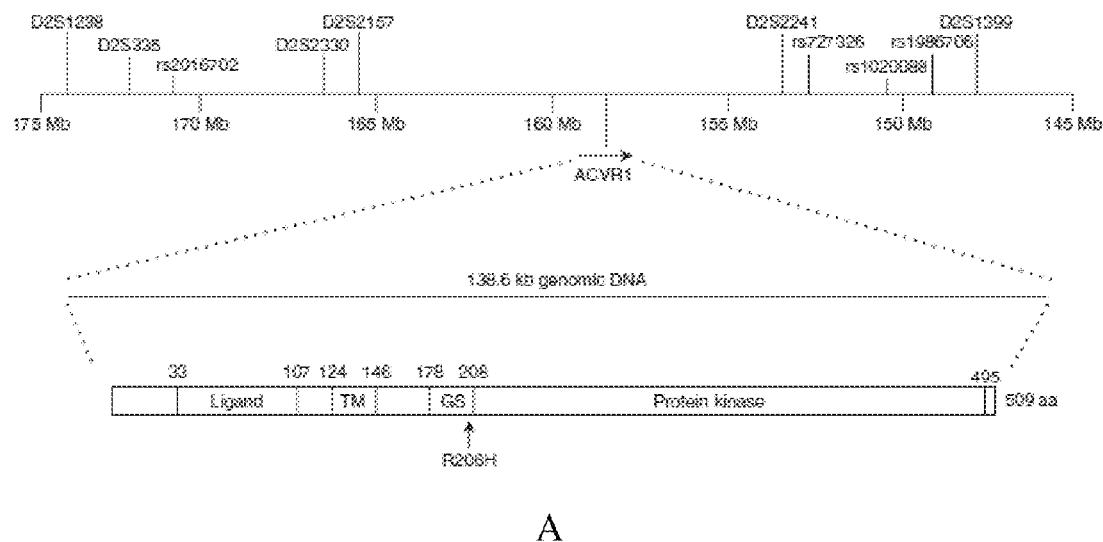
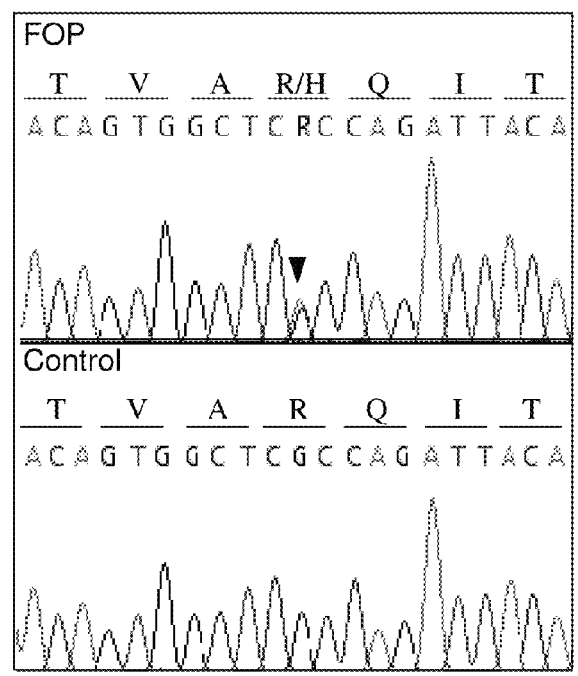
Figure 3

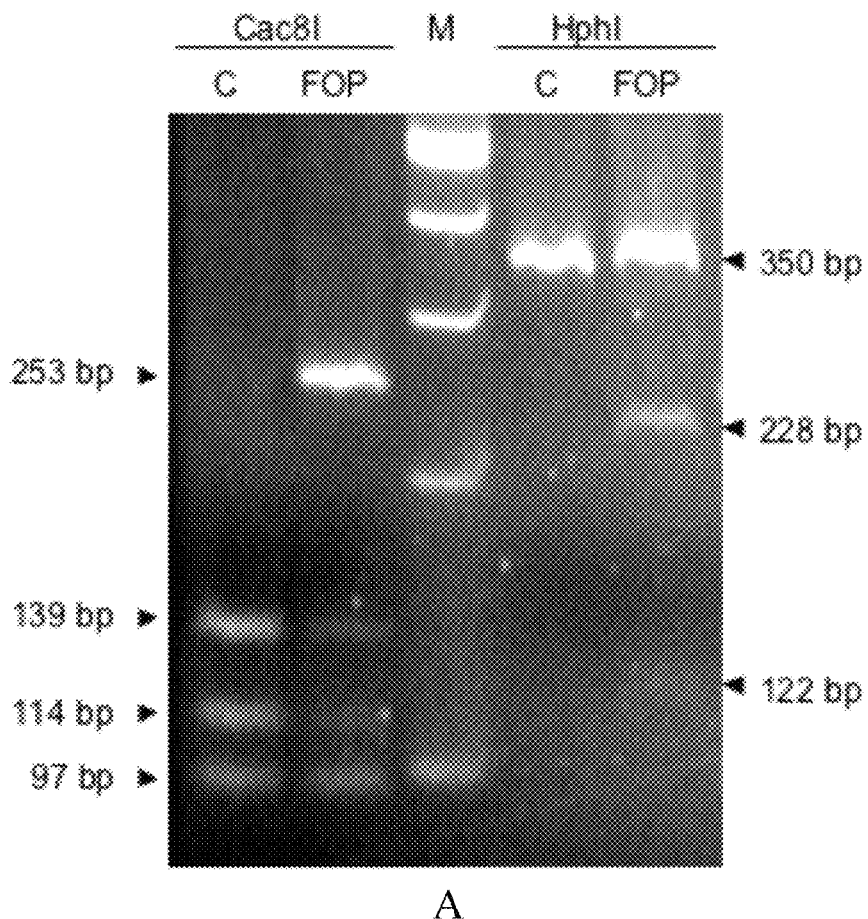

A

```
FOP mutation 178 STLADLLDHSCTSGSGSGLPFLVQRTVAHQI 208

H. sapiens      STLADLLDHSCTSGSGSGLPFLVQRTVARQI
M. musculus     STLAELLDHSCTSGSGSGLPFLVQRTVARQI
R. norvegicus   STLAELLDHSCTSGSGSGLPFLVQRTVARQI
C. familiaris   STLADLLDHSCTSGSGSGLPFLVQRTVARQI
B. taurus       STLADLLDHSCTSGSGSGLPFLVQRTVARQI
G. gallus       STLADLLDHSCTSGSGSGLPFLVQRTVARQI
X. laevis       STLAEMLDHSCTSGSGSGLPFLVQRTVARQI
D. rerio        STLADLMDHSCTSGSGSGLPFLVQRTVARQI
F. rubripes     STLADLLDHSCTSGSGSGLPFLVQRTVARQI
                ****__ *********************** 
```

```
ACVR1 FOP mutation  178  STLADLLDHSCTSGSGSGLPFLVQRTVAHQITLLE  212

ACVR1                    STLADLLDHSCTSGSGSGLPFLVQRTVARQITLLE  212
ACVR1B                   KTLQDLVYDLSTSGSGSGLPLFVQRTVARTIVLQE  211
ACVR1C                   KTLKDLIYDVTASGSGSGLPLLVQRTIARTIVLQE  199
ACVRL1                   TMLGDLLDSDCTTGSGSGLPFLVQRTVARQVALVE  206
                         __*_**_____*******__***_**___*_*

BMPR1A                   ESLKDLIDQSQSSGSGSGLPLLVQRTIAKQIQMVR  238
BMPR1B                   ESLRDLIEQSQSSGSGSGLPLLVQRTIAKQIQMVK  208
                         ***_***_***********************

TGFBR1              114  ---------------TGLPLLVQRTIARTIVLQE  132
                                        ***__****_*_____
```

Figure 6

```
Wild-type ACVR1    5'- AACAGTGGCTCGCCAGATTACACTGTTGGAGT -3'

Mutant ACVR1       5'- AACAGTGGCTCACCAGATTACACTGTTGGAGT -3'

A7         5'- UGGCUCACCAGAUUACACUUU -3'
        A8         5'- GUGGCUCACCAGAUUACACUU -3'
        A9         5'- AGUGGCUCACCAGAUUACAUU -3'
        A10        5'- CAGUGGCUCACCAGAUUACUU -3'
        A11        5'- ACAGUGGCUCACCAGAUUAUU -3'
        A12        5'- AACAGUGGCUCACCAGAUUUU -3'
        A10C19A    5'- CAGUGGCUCACCAGAUUAAUU -3'
        A10C19G    5'- CAGUGGCUCACCAGAUUAGUU -3'
```

Figure 8

SIRNA-BASED THERAPY OF FIBRODYPLASIA OSSIFICANS PROGRESSIVA (FOP)

CROSS-REFERENCE TO RELATED APPLICATIONS

This application is a Continuation-In-Part of U.S. application Ser. No. 12/296,275, filed Jun. 15, 2009, which is a National Stage Entry of International Application Number PCT/US07/09357, filed Apr. 17, 2007, claiming priority of U.S. Provisional Application Ser. No. 60/792,646, filed Apr. 18, 2006, each of which is hereby incorporated by reference in its entirety.

FIELD OF INVENTION

This invention is directed to mutated Activin A type I receptor proteins (ACVR1) and isolated nucleic acids encoding same. The invention also relates to compositions and methods for siRNA-based regulation of mutated ACVR1 expression in the treatment of Fibrodysplasia Ossificans Progressiva (FOP).

BACKGROUND OF THE INVENTION

The formation of bone where it is neither needed nor wanted can lead to devastating consequences. Fibrodysplasia Ossificans Progressiva (FOP, OMIM 135100), also known as Myositis Ossificans Progressiva, is the most severe and disabling disorder of extra-skeletal (heterotopic) ossification in humans. Heterotopic ossification in FOP begins in childhood and can be induced by trauma, or may occur without warning. Bone formation is episodic and progressive, leading to extra-articular ankylosis of all major joints of the axial and appendicular skeleton, rendering movement impossible (FIG. 1a).

The earliest pathological finding in FOP is perivascular lymphocytic infiltration into normal-appearing skeletal muscle, followed by muscle-cell degeneration and highly vascular fibroproliferative soft tissue swelling. The fibroproliferative lesions evolve, through an endochondral process, into mature lamellar bone with marrow elements. Heterotopic ossifications are usually first detected around the spine and proximal extremities, then at multiple other places, which leads to dysfunction of articulations and often premature death.

FOP is a rare condition; the prevalence is ~0.6/1 million live births. Reproductive fitness is low, and most cases appear to arise by spontaneous mutation. There is no effective treatment, and soft-tissue trauma (eg, biopsies, surgical procedures, intramuscular injections, or mandibular blocks for dental procedures) and viral illnesses are likely to induce episodes of rapidly progressive heterotopic ossification, with resultant permanent loss of motion in the affected area. Diagnostic errors with FOP are thought to be common and often associated with inappropriate and harmful diagnostic and therapeutic procedures Therefore, reliable methods are needed for an early diagnosis, as well as treatment methods, thereby providing a foundation for development of treatments not only for FOP, but also for the more common disorders of osteogenesis.

SUMMARY OF THE INVENTION

In one aspect, provided herein are isolated nucleic acids, the isolated nucleic acids encoding mutated Activin A type I receptor proteins (ACVR1), represented by SEQ ID NOs: 21-25 and 27-32 or a combination thereof.

In another aspect, provided herein are oligonucleotides of at least 15 nucleotides capable of specifically hybridizing with a sequence of a nucleic acid encoding the mutated Activin A type I receptor protein (ACVR1) set forth in SEQ ID NOs. 21-25 and 27-32, or a combination thereof.

In a further aspect, provided herein are allele-specific siRNAs, the allele-specific siRNAs comprise a siRNA specific against a nucleic acid encoding a mutated Activin A type I receptor (ACVR1) represented by SEQ ID NOs: 21-25 and 27-32 or their combination relative to a nucleic acid encoding wild-type Activin A type I receptor protein (ACVR1) as set forth in SEQ ID NO. 26. In yet a further aspect, provided herein are siRNAs, siRNAs comprise a siRNA specific against a nucleic acid encoding a wild type (e.g., the human protein as set forth in SEQ ID NO. 26) Activin A type I receptor (ACVR1).

In an additional aspect, provided herein are methods of treating Fibrodysplasia Ossificans Progressiva (FOP) in a subject, the methods including the step of: administering to said subject a therapeutically effective amount of a siRNA specific against a nucleic acid encoding a mutated Activin A type I receptor (ACVR1) represented by SEQ ID NOs: 21-25 and 27-32 or their combination relative to a nucleic acid encoding wild-type Activin A type I receptor protein (ACVR1) as set forth in SEQ ID NO. 26. In yet an additional aspect, provided herein are methods of treating Fibrodysplasia Ossificans Progressiva (FOP) in a subject, the methods including the step of: administering to said subject a therapeutically effective amount of a siRNA specific against a nucleic acid encoding a wild type (e.g., the human protein as set forth in SEQ ID NO. 26) Activin A type I receptor (ACVR1).

In yet another aspect, provided herein are methods of treating a pathology associated with heterotopic ossification in a subject, the methods including the step of: administering to said subject a therapeutically effective amount of a siRNA specific against a nucleic acid encoding a mutated Activin A type I receptor (ACVR1) represented by SEQ ID NOs: 21-25 and 27-32 or their combination relative to a nucleic acid encoding wild-type Activin A type I receptor protein (ACVR1) as set forth in SEQ ID NO. 26. In an other aspect, provided herein are methods of treating a pathology associated with heterotopic ossification in a subject, the methods including the step of: administering to said subject a therapeutically effective amount of a siRNA specific against a nucleic acid encoding a wild type (e.g., the human protein as set forth in SEQ ID NO. 26) Activin A type I receptor (ACVR1).

Unless otherwise defined, all technical and scientific terms used herein have the same meaning as commonly understood by one of ordinary skill in the art to which this invention belongs. Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description. It is also contemplated that whenever appropriate, any embodiment of the present invention can be combined with one or more other embodiments of the present invention, even though the embodiments are described under different aspects of the present invention.

BRIEF DESCRIPTION OF THE DRAWINGS

The invention will be better understood from a reading of the following detailed description taken in conjunction with the drawings in which like reference designators are used to designate like elements, and in which:

FIG. 1 shows characteristic clinical features of FOP. (A) Extensive heterotopic bone formation typical of FOP is seen by 3-dimensional reconstructed computed tomography (CT) scan of the back of a twelve-year-old child. (B) Anteroposterior radiograph of the feet of a three-year-old child shows symmetrical great toe malformations;

FIG. 3 shows the identification of Arg206His mutations in the ACVR1 gene in patients with FOP. (A) The chromosome 2q FOP critical genomic region spans ~23.9 Mb between markers rsl02O088 (centromeric) at 150,654,341 bp and D2S1238 (telomeric) at 174,505,230 bp as annotated by UCSC GenomeBrowser. The ACVR1 gene spans—138.6 kb of genomic DNA (chromosome 2: 158,418,469-158,557, 131). ACVR1 encodes a 509 amino acid protein that contains a ligand binding region, a transmembrane (TM) domain, a glycine-serine (GS) rich domain, and a protein kinase domain. The numbers above the protein representation indicate the amino acids included in each identified domain. The position of the Arg206His mutation in the GS region is indicated by an arrow. The schematics are drawn approximately to scale. (B) Direct DNA sequence analysis of the ACVR1 candidate gene in the chromosome 2q linkage region revealed the identical heterozygous mutation (R206H; at cDNA nucleotide position c.617G>A) in all examined FOP patients. The nucleotide and amino acid sequences are shown for a representative affected individual (top) (SEQ ID NOs: 34 and 33, respectively) and an unaffected control (bottom) (SEQ ID NOs: 36 and 35, respectively). In the nucleotide sequence, R=A or G; in the amino acid sequence R=arginine and H=histidine;

FIG. 4 shows (A) the G>A mutation forms a new HphI site and eliminates a Cac8I site in the mutant allele. PCR product (350 bp) from control DNA (C) is undigested by HphI; the heterozygous mutation in patient DNA results in the undigested product from the normal allele and Hphl-digested products (228 and 122 bp) from the mutant allele (FOP). The same PCR product from control DNA is digested by Cac8I to produce three bands (139, 114, and 97 bp) while the mutant allele produces two bands (253 and 97 bp). (B) ACVR1 codon 206 is highly conserved among species. The Arg206His FOP mutation (SEQ ID NO: 37) in the ACVR1 gene (also known as Alk2) occurs within the highly conserved GS domain (amino acids 178-208 in mammals; SEQ ID NOs: 38-41). An * below the sequence indicates an identical amino acid at the corresponding position of ACVR1/ALK2 protein in various species. Clustal W was used for multiple protein sequence alignment;

FIG. 6 shows amino acid homologies among human ACVR1 family members and conservation of the GS domain in human type I BMP/Activin receptors. Protein sequences were aligned using the Clustal W algorithm. At the position analogous to ACVR1 Arg206, there is an arginine (R) in human type I Activin receptors (ACVR1 (SEQ ID NO: 43)), ACVR1B (SEQ ID NO: 44), ACVR1C (SEQ ID NO: 45), ACVRL1 (SEQ ID NO: 46)) and TGFβR1 (SEQ ID NO: 49). Of these receptors, only ACVR1 has been found to mediate BMP signaling. By contrast, two other BMP type I receptors (BMPRIA (SEQ ID NO: 47)) and BMPRIB (SEQ ID NO: 48)) have a lysine (K) at the position analogous to ACVR1 Arg206. Like arginine, lysine is a positively charged amino acid and is expected to maintain similar function, however this amino acid difference may contribute to receptor specificity and differences in regulation of downstream signaling;

FIG. 8 shows ASP-siRNA duplexes used for targeted suppression of mutant c.617A allele. Sequence of wild-type (c.617G) (SEQ ID NO: 51) and mutant (c.617A) (SEQ ID NO: 52) ACVR1 alleles (top). The nucleotide that is mutated in FOP patients (A7-A12; respectively, SEQ ID NO: 53-SEQ ID NO: 58) is highlighted in bold (bottom). Only sense (passenger)-strand is shown, with UU representing dTdT overhangs at 3' end of duplexes. Both sense and anti-sense strands were synthesized and annealed without further chemical modifications of duplexes. Bold nucleotide represents mutant c.617A allele within each duplex. siRNA duplexes A10C19A (SEQ ID NO: 59) and A10C19G (SEQ ID NO: 60) contain an additional mismatch at the 19th nucleotide on the sense strand (also in bold)

Figure 2A:
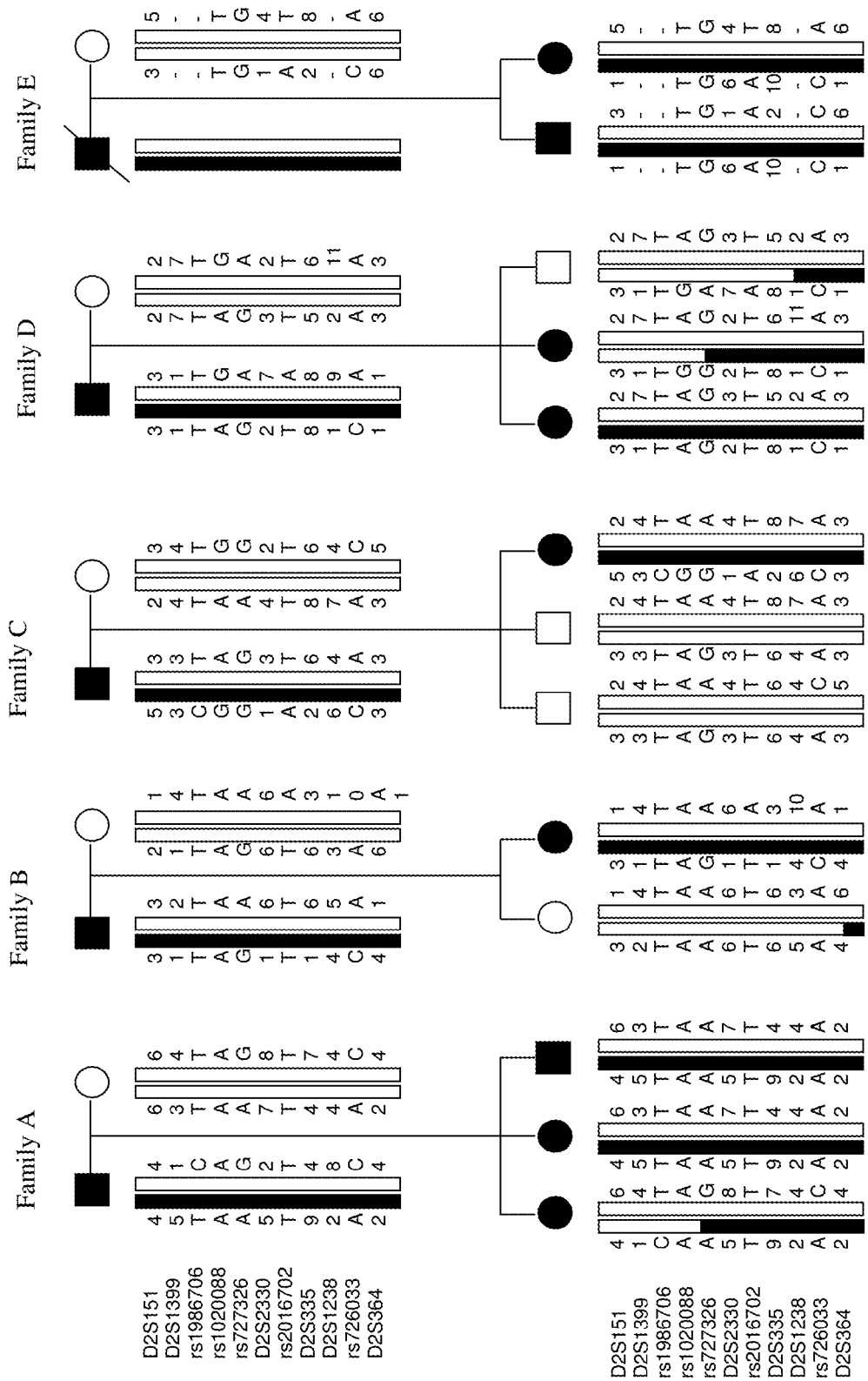
FIG. 2 shows linkage mapping in five pedigrees with classic FOP features. (A) Marker haplotypes on chromosome 2q23-24 that are linked to FOP are indicated by black bars. Microsatellite markers and SNPs are listed at left from centromere to telomere (top to bottom). Haplotypes are interpreted by minimizing recombinants. In each haplotype pair, paternal haplotypes are to the left and maternal to the right. Circles represent females, squares represent males, and filled symbols indicate the presence of FOP. A diagonal line through a symbol indicates that the individual is deceased and unavailable for analysis. (B) Combined multipoint lod plot for markers in the chromosome 2 FOP linkage region. Markers (shown in a) are on the X-axis at approximate relative distances measured in megabases (Mb). Marker positions were obtained from the UCSC GenomeBrowser.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

This invention is directed to mutated Activin A type I receptor proteins (ACVR1) and isolated nucleic acids encoding same. The invention also relates to the use of mutated ACVR1 in the diagnosis and treatment of Fibrodysplasia Ossificans Progressiva (FOP).

In a further aspect, provided herein are allele-specific siRNAs, the allele-specific siRNAs comprise In a further aspect, provided herein are allele-specific siRNAs, the allele-specific siRNAs comprise a siRNA specific against a nucleic acid encoding a mutated Activin A type I receptor (ACVR1) represented by SEQ ID NOs: 21-25 and 27-32 or their combination relative to a nucleic acid encoding wild-type Activin A type I receptor protein (ACVR1) as set forth in SEQ ID NO. 26. In yet a further aspect, provided herein are siRNAs, siRNAs comprise a siRNA specific against a nucleic acid encoding a wild type (e.g., the human protein as set forth in SEQ ID NO. 26) Activin A type I receptor (ACVR1).

In an additional aspect, provided herein are methods of treating Fibrodysplasia Ossificans Progressiva (FOP) in a subject, the methods including the step of: administering to said subject a therapeutically effective amount of a siRNA specific against a nucleic acid encoding a mutated Activin A type I receptor (ACVR1) represented by SEQ ID NOs: 21-25 and 27-32 or their combination relative to a nucleic acid encoding wild-type Activin A type I receptor protein (ACVR1) as set forth in SEQ ID NO. 26. In yet an additional aspect, provided herein are methods of treating Fibrodysplasia Ossificans Progressiva (FOP) in a subject, the methods including the step of: administering to said subject a therapeutically effective amount of a siRNA specific against a nucleic acid encoding a wild type (e.g., the human protein as set forth in SEQ ID NO. 26) Activin A type I receptor (ACVR1).

In yet another aspect, provided herein are methods of treating a pathology associated with heterotopic ossification in a subject, the methods including the step of: administering to said subject a therapeutically effective amount of a siRNA specific against a nucleic acid encoding a mutated Activin A type I receptor (ACVR1) represented by SEQ ID NOs: 21-25 and 27-32 or their combination relative to a nucleic acid encoding wild-type Activin A type I receptor protein (ACVR1) as set forth in SEQ ID NO. 26. In an other aspect, provided herein are methods of treating a pathology associated with heterotopic ossification in a subject, the methods including the step of: administering to said subject a therapeutically effective amount of a siRNA specific against a nucleic acid encoding a wild type (e.g., the human protein as set forth in SEQ ID NO. 26) Activin A type I receptor (ACVR1).

In one embodiment, the mutated nucleic acid is comprised of the nucleic acid sequence encoding ACVR1 Arg206His mutant sequence (R206H; c.617G>A) of:

(SEQ ID NO. 21)
MVDGVMILPVLIMIALPSPSMEDEKPKVNPKLYMCVCEGLSCGNEDH

CEGQQCFSSLSINDGFHVYQKGCFQVYEQGKMTCKTPPSPGQAVECC

QGDWCNRNITAQLPTKGKSFPGTQNFHLEVGLIILSVVFAVCLLACL

LGVALRKFKRRNQERLNPRDVEYGTIEGLITTNVGDSTLADLLDHSC

TSGSGSGLPFLVQRTVAHQITLLECVGKGRYGEVWRGSWQGENVAVK

IFSSRDEKSWFRETELYNTVMLRHENILGFIASDMTSRHSSTQLWLI

THYHEMGSLYDYLQLTTLDTVSCLRIVLSIASGLAHLHIEIFGTQGK

PAIAHRDLKSKNILVKKNGQCCIADLGLAVMHSQSTNQLDVGNNPRV

GTKRYMAPEVLDETIQVDCFDSYKRVDIWAFGLVLWEVARRMVSNGI

VEDYKPPFYDVVPNDPSFEDMRKVVCVDQQRPNIPNRWFSDPTLTSL

AKLMKECWYQNPSARLTALRIKKTLTKIDNSLDKLKTDC

In one embodiment, the mutated nucleic acid is comprised of the nucleic acid sequence encoding ACVR1Gln207Glu mutant sequence (Q207E; c.619C>G) of:

(SEQ ID NO. 22)
MVDGVMILPVLIMIALPSPSMEDEKPKVNPKLYMCVCEGLSCGNEDH

CEGQQCFSSLSINDGFHVYQKGCFQVYEQGKMTCKTPPSPGQAVECC

QGDWCNRNITAQLPTKGKSFPGTQNFHLEVGLIILSVVFAVCLLACL

LGVALRKFKRRNQERLNPRDVEYGTIEGLITTNVGDSTLADLLDHSC

TSGSGSGLPFLVQRTVAREITLLECVGKGRYGEVWRGSWQGENVAVK

IFSSRDEKSWFRETELYNTVMLRHENILGFIASDMTSRHSSTQLWLI

THYHEMGSLYDYLQLTTLDTVSCLRIVLSIASGLAHLHIEIFGTQGK

PAIAHRDLKSKNILVKKNGQCCIADLGLAVMHSQSTNQLDVGNNPRV

GTKRYMAPEVLDETIQVDCFDSYKRVDIWAFGLVLWEVARRMVSNGI

VEDYKPPFYDVVPNDPSFEDMRKVVCVDQQRPNIPNRWFSDPTLTSL

AKLMKECWYQNPSARLTALRIKKTLTKIDNSLDKLKTDC

In one embodiment, the mutated nucleic acid is comprised of the nucleic acid sequence encoding ACVR1Gly328Trp mutant sequence (G328W; c.982G>T) of:

(SEQ ID NO. 23)
MVDGVMILPVLIMIALPSPSMEDEKPKVNPKLYMCVCEGLSCGNEDHC

EGQQCFSSLSINDGFHVYQKGCFQVYEQGKMTCKTPPSPGQAVECCQG

DWCNRNITAQLPTKGKSFPGTQNFHLEVGLIILSVVFAVCLLACLLGV

ALRKFKRRNQERLNPRDVEYGTIEGLITTNVGDSTLADLLDHSCTSGS

GSGLPFLVQRTVARQITLLECVGKGRYGEVWRGSWQGENVAVKIFSSR

DEKSWFRETELYNTVMLRHENILGFIASDMTSRHSSTQLWLITHYHEM

GSLYDYLQLTTLDTVSCLRIVLSIASGLAHLHIEIFGTQWKPAIAHRD
LKSKNILVKKNGQCCIADLGLAVMHSQSTNQLDVGNNPRVGTKRYMAP
EVLDETIQVDCFDSYKRVDIWAFGLVLWEVARRMVSNGIVEDYKPPFY
DVVPNDPSFEDMRKVVCVDQQRPNIPNRWFSDPTLTSLAKLMKECWYQ
NPSARLTALRIKKTLTKIDNSLDKLKTDC

In one embodiment, the mutated nucleic acid is comprised of the nucleic acid sequence encoding ACVR1Gly328Glu mutant sequence (G328E; c.983G>A) of:

(SEQ ID NO. 24)
MVDGVMILPVLIMIALPSPSMEDEKPKVNPKLYMCVCEGLSCGNEDH
CEGQQCFSSLSINDGFHVYQKGCFQVYEQGKMTCKTPPSPGQAVECC
QGDWCNRNITAQLPTKGKSFPGTQNFHLEVGLIILSVVFAVCLLACL
LGVALRKFKRRNQERLNPRDVEYGTIEGLITTNVGDSTLADLLDHSC
TSGSGSGLPFLVQRTVARQITLLECVGKGRYGEVWRGSWQGENVAVK
IFSSRDEKSWFRETELYNTVMLRHENILGFIASDMTSRHSSTQLWLI
THYHEMGSLYDYLQLTTLDTVSCLRIVLSIASGLAHLHIEIFGTQEK
PAIAHRDLKSKNILVKKNGQCCIADLGLAVMHSQSTNQLDVGNNPRV
GTKRYMAPEVLDETIQVDCFDSYKRVDIWAFGLVLWEVARRMVSNGI
VEDYKPPFYDVVPNDPSFEDMRKVVCVDQQRPNIPNRWFSDPTLTSL
AKLMKECWYQNPSARLTALRIKKTLTKIDNSLDKLKTDC

In one embodiment, the mutated nucleic acid is comprised of the nucleic acid sequence encoding ACVR1Gly356Asp mutant sequence (G356D; c.1067G>A) of:

(SEQ ID NO. 25)
MVDGVMILPVLIMIALPSPSMEDEKPKVNPKLYMCVCEGLSCGNED
HCEGQQCFSSLSINDGFHVYQKGCFQVYEQGKMTCKTPPSPGQAVE
CCQGDWCNRNITAQLPTKGKSFPGTQNFHLEVGLIILSVVFAVCLL
ACLLGVALRKFKRRNQERLNPRDVEYGTIEGLITTNVGDSTLADLL
DHSCTSGSGSGLPFLVQRTVARQITLLECVGKGRYGEVWRGSWQGE
NVAVKIFSSRDEKSWFRETELYNTVMLRHENILGFIASDMTSRHSS
TQLWLITHYHEMGSLYDYLQLTTLDTVSCLRIVLSIASGLAHLHIE
IFGTQGKPAIAHRDLKSKNILVKKNGQCCIADLDLAVMHSQSTNQL
DVGNNPRVGTKRYMAPEVLDETIQVDCFDSYKRVDIWAFGLVLWEV
ARRMVSNGIVEDYKPPFYDVVPNDPSFEDMRKVVCVDQQRPNIPNR
WFSDPTLTSLAKLMKECWYQNPSARLTALRIKKTLTKIDNSLDKLK
TDC.

In one embodiment, the mutated nucleic acid is comprised of the nucleic acid sequence encoding ACVR1Ala15Gly mutant sequence (A15G; c.44C>G) of:

(SEQ ID NO. 27)
MVDGVMILPVLIMIGLPSPSMEDEKPKVNPKLYMCVCEGLSCGNEDH
CEGQQCFSSLSINDGFHVYQKGCFQVYEQGKMTCKTPPSPGQAVECCQ
GDWCNRNITAQLPTKGKSFPGTQNFHLEVGLIILSVVFAVCLLACLL
GVALRKFKRRNQERLNPRDVEYGTIEGLITTNVGDSTLADLLDHSCT
SGSGSGLPFLVQRTVARQITLLECVGKGRYGEVWRGSWQGENVAVKI
FSSRDEKSWFRETELYNTVMLRHENILGFIASDMTSRHSSTQLWLIT
HYHEMGSLYDYLQLTTLDTVSCLRIVLSIASGLAHLHIEIFGTQGKP
AIAHRDLKSKNILVKKNGQCCIADLGLAVMHSQSTNQLDVGNNPRVG
TKRYMAPEVLDETIQVDCFDSYKRVDIWAFGLVLWEVARRMVSNGIV
EDYKPPFYDVVPNDPSFEDMRKVVCVDQQRPNIPNRWFSDPTLTSLA
KLMKECWYQNPSARLTALRIKKTLTKIDNSLDKLKTDC.

In one embodiment, the mutated nucleic acid is comprised of the nucleic acid sequence encoding ACVR1 wherein 3 nucleotide deletion replaces Pro197 and Phe 198 with one Leu residue Pro197, Phe198>Leu mutant sequence (P197, F198>L; c.590-592delCTT) of:

(SEQ ID NO. 28)
MVDGVMILPVLIMIALPSPSMEDEKPKVNPKLYMCVCEGLSCGNEDHC
EGQQCFSSLSINDGFHVYQKGCFQVYEQGKMTCKTPPSPGQAVECCQG
DWCNRNITAQLPTKGKSFPGTQNFHLEVGLIILSVVFAVCLLACLLGV
ALRKFKRRNQERLNPRDVEYGTIEGLITTNVGDSTLADLLDHSCTSGS
GSGLLLVQRTVARQITLLECVGKGRYGEVWRGSWQGENVAVKIFSSRD
EKSWFRETELYNTVMLRHENILGFIASDMTSRHSSTQLWLITHYHEMG
SLYDYLQLTTLDTVSCLRIVLSIASGLAHLHIEIFGTQGKPAIAHRDL
KSKNILVKKNGQCCIADLGLAVMHSQSTNQLDVGNNPRVGTKRYMAPE
VLDETIQVDCFDSYKRVDIWAFGLVLWEVARRMVSNGIVEDYKPPFYD
VVPNDPSFEDMRKVVCVDQQRPNIPNRWFSDPTLTSLAKLMKECWYQN
PSARLTALRIKKTLTKIDNSLDKLKTDC.

In another embodiment, the mutated nucleic acid is comprised of the nucleic acid sequence encoding ACVR1Gln207Glu mutant sequence (Q207E; c.619C>G) of:

(SEQ ID NO. 29)
MVDGVMILPVLIMIALPSPSMEDEKPKVNPKLYMCVCEGLSCGNEDHC
EGQQCFSSLSINDGFHVYQKGCFQVYEQGKMTCKTPPSPGQAVECCQG
DWCNRNITAQLPTKGKSFPGTQNFHLEVGLIILSVVFAVCLLACLLGV
ALRKFKRRNQERLNPRDVEYGTIEGLITTNVGDSTLADLLDHSCTSGS
GSGLPFLVQRTVAREITLLECVGKGRYGEVWRGSWQGENVAVKIFSSR
DEKSWFRETELYNTVMLRHENILGFIASDMTSRHSSTQLWLITHYHEM
GSLYDYLQLTTLDTVSCLRIVLSIASGLAHLHIEIFGTQGKPAIAHRD
LKSKNILVKKNGQCCIADLGLAVMHSQSTNQLDVGNNPRVGTKRYMAP
EVLDETIQVDCFDSYKRVDIWAFGLVLWEVARRMVSNGIVEDYKPPFY
DVVPNDPSFEDMRKVVCVDQQRPNIPNRWFSDPTLTSLAKLMKECWYQ
NPSARLTALRIKKTLTKIDNSLDKLKTDC.

In another embodiment, the mutated nucleic acid is comprised of the nucleic acid sequence encoding ACVR1 Arg258Ser mutant sequence (R258S; c.744G>C) of:

```
                                            (SEQ ID NO. 30)
MVDGVMILPVLIMIALPSPSMEDEKPKVNPKLYMCVCEGLSCGNEDHC

EGQQCFSSLSINDGFHVYQKGCFQVYEQGKMTCKTPPSPGQAVECCQG

DWCNRNITAQLPTKGKSFPGTQNFHLEVGLIILSVVFAVCLLACLLGV

ALRKFKRRNQERLNPRDVEYGTIEGLITTNVGDSTLADLLDHSCTSGS

GSGLPFLVQRTVARQITLLECVGKGRYGEVWRGSWQGENVAVKIFSSR

DEKSWFRETELYNTVMLSHENILGFIASDMTSRHSSTQLWLITHYHEM

GSLYDYLQLTTLDTVSCLRIVLSIASGLAHLHIEIFGTQGKPAIAHRD

LKSKNILVKKNGQCCIADLGLAVMHSQSTNQLDVGNNPRVGTKRYMAP

EVLDETIQVDCFDSYKRVDIWAFGLVLWEVARRMVSNGIVEDYKPPFY

DVVPNDPSFEDMRKVVCVDQQRPNIPNRWFSDPTLTSLAKLMKECWYQ

NPSARLTALRIKKTLTKIDNSLDKLKTDC.
```

In one embodiment, the mutated nucleic acid is comprised of the nucleic acid sequence encoding ACVR1Gly328Arg mutant sequence (G328R; c.982G>A) of:

```
                                            (SEQ ID NO. 31)
MVDGVMILPVLIMIALPSPSMEDEKPKVNPKLYMCVCEGLSCGNEDHC

EGQQCFSSLSINDGFHVYQKGCFQVYEQGKMTCKTPPSPGQAVECCQG

DWCNRNITAQLPTKGKSFPGTQNFHLEVGLIILSVVFAVCLLACLLGV

ALRKFKRRNQERLNPRDVEYGTIEGLITTNVGDSTLADLLDHSCTSGS

GSGLPFLVQRTVARQITLLECVGKGRYGEVWRGSWQGENVAVKIFSSR

DEKSWFRETELYNTVMLRHENILGFIASDMTSRHSSTQLWLITHYHEM

GSLYDYLQLTTLDTVSCLRIVLSIASGLAHLHIEIFGTQRKPAIAHRD

LKSKNILVKKNGQCCIADLGLAVMHSQSTNQLDVGNNPRVGTKRYMAP

EVLDETIQVDCFDSYKRVDIWAFGLVLWEVARRMVSNGIVEDYKPPFY

DVVPNDPSFEDMRKVVCVDQQRPNIPNRWFSDPTLTSLAKLMKECWYQ

NPSARLTALRIKKTLTKIDNSLDKLKTDC.
```

In one embodiment, the mutated nucleic acid is comprised of the nucleic acid sequence encoding ACVR1 Arg375Pro mutant sequence (R375P; c.1124G>C) of:

```
                                            (SEQ ID NO. 32)
MVDGVMILPVLIMIALPSPSMEDEKPKVNPKLYMCVCEGLSCGNEDH

CEGQQCFSSLSINDGFHVYQKGCFQVYEQGKMTCKTPPSPGQAVECC

QGDWCNRNITAQLPTKGKSFPGTQNFHLEVGLIILSVVFAVCLLACL

LGVALRKFKRRNQERLNPRDVEYGTIEGLITTNVGDSTLADLLDHSC

TSGSGSGLPFLVQRTVARQITLLECVGKGRYGEVWRGSWQGENVAVK

IFSSRDEKSWFRETELYNTVMLRHENILGFIASDMTSRHSSTQLWLI

THYHEMGSLYDYLQLTTLDTVSCLRIVLSIASGLAHLHIEIFGTQGK

PAIAHRDLKSKNILVKKNGQCCIADLGLAVMHSQSTNQLDVGNNPPV

GTKRYMAPEVLDETIQVDCFDSYKRVDIWAFGLVLWEVARRMVSNGI

VEDYKPPFYDVVPNDPSFEDMRKVVCVDQQRPNIPNRWFSDPTLTSL

AKLMKECWYQNPSARLTALRIKKTLTKIDNSLDKLKTDC.
```

Fibrodysplasia Ossificance Progressiva (FOP) is the most severe and disabling disorder of extra-skeletal (heterotopic) ossification in humans. Heterotopic ossification in FOP begins in childhood and can be induced by trauma or may occur without warning. Bone formation is episodic, progressive, or extensive, leading to the extra-articular ankylosis of all the major joints of the axial and appendicular skeleton, rendering movement impossible (FIG. 1a). Flareups of FOP arise and progress, in a well-defined spatial pattern that result in ribbons, or sheets, or plates of bone, that fuse the joints of the axial and appendicular skeleton, entombing the patient in a "second skeleton" of heterotopic bone. One of the more readily recognized skeletal malformations in FOP patients are great toe malformations of metatarsals and proximal phalanges that occurs along with microdactyl), fused interphalangeal joints, and hallux valgus deviations at the metatarsophalangeal joints (FIG. 1b). The severe disability of FOP results in low reproductive fitness and few examples of inheritance of FOP are known. Death often results by the fifth decade from thoracic insufficiency syndrome. Provided herein are methods, compositions and kits for use in treating or providing early diagnosis of FOP in subjects.

Analysis of ACVR1 mRNA expression by RT-PCR and sequencing shows that both mutant and normal mRNAs are expressed in FOP cells, suggesting that the mutation effects are not due to haploinsufficiency, but are due to altered protein function. Constitutive ACVR1 expression in embryonic chick limbs induced expansion of chondrogenic anlage indicating that ACVR1 signaling alters cell fate and induces undifferentiated mesenchyme to form cartilage. Enhanced ACVR1 activation in FOP results in increased expression of BMP transcriptional targets in FOP cells.

According to one aspect of the invention, and in one embodiment, the invention provides an isolated nucleic acid encoding a mutated Activin A type I receptor protein (ACVR1), wherein the nucleic acid enhances activity of bone morphogenetic protein (BMP) receptor and/or signaling and is pathognomonic of Fibrodysplasia Ossificans Progressiva (FOP).

In another embodiment, the isolated amino acid sequence of the protein has a sequence having at least 82% similarity with any one of the amino acid sequence of SEQ ID NO's 21 to 32 or their combination. In another embodiment, the isolated amino acid sequence of the protein has a sequence having at least 85% similarity with any one of the amino acid sequence of SEQ ID NO's 21 to 32 or their combination. In another embodiment, the amino acid sequence has a nucleotide sequence having at least 90% similarity with any one of the amino acid sequence of SEQ ID NO's 21 to 32 or their combination. In another embodiment, the amino acid sequence has a nucleotide sequence having at least 95% similarity with any one of the amino acid sequence of SEQ ID NO's 21 to 32 or their combination. In another embodiment, the amino acid sequence has a nucleotide sequence having 100% similarity with any one of the amino acid sequence of SEQ ID NO's 21 to 32 or their combination. In another embodiment, the isolated nucleic acid used in the invention is encoded by DNA, cDNA, genomic DNA, RNA, or a PCR product.

The invention further encompasses amino acid molecules that differ from any one of the amino acid sequence of SEQ ID NO's 21 to 32 or their combination, due to degeneracy of the genetic code of their encoding gene and thus encode the same mutated Activin A type I receptor protein (ACVR1) as the amino acid sequence shown in any one of the amino acid sequence of SEQ ID NO's 21 to 32 or their combination. It will be appreciated by those skilled in the art that DNA sequence polymorphisms that lead to changes in the amino acid sequences of the mutated Activin A type I receptor protein (ACVR1) may exist within a population (e.g., the human population). Such genetic polymorphism in the gene encoding mutated Activin A type I receptor protein (ACVR1), may exist among individuals within a population due to natural allelic variation. In one embodiment, an allele is one of a group of genes which occur alternatively at a given genetic locus. Such natural allelic variations can typically result in 1-5% variance in the nucleotide sequence of the gene encoding mutated Activin A type I receptor protein (ACVR1).

Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms in the mutated Activin A type I receptor protein (ACVR1), that are the result of natural allelic variation and that do not alter the functional activity of the mutated Activin A type I receptor protein (ACVR1) are intended to be within the scope of the embodiments described herein. Moreover, nucleic acid molecules encoding the mutated Activin A type I receptor proteins (ACVR1) from other species (the mutated Activin A type I receptor protein (ACVR1) homologues), which have a nucleotide sequence which differs from that of a human Activin A type I receptor protein (ACVR1), are intended to be within the scope of the invention. Nucleic acid molecules corresponding to natural allelic variants and homologues of the mutated Activin A type I receptor protein (ACVR1) cDNA as described herein, can be isolated based on their identity to the human mutated Activin A type I receptor protein (ACVR1) nucleic acids disclosed herein using human cDNAs, or a portion thereof, as a hybridization probe according to standard hybridization techniques under stringent hybridization conditions. For example, splice variants of the human and mouse mutated Activin A type I receptor protein (ACVR1) cDNA can be isolated based on identity to human and mouse mutated Activin A type I receptor protein (ACVR1).

As used herein, the term "hybridizes under stringent conditions" is intended to describe conditions for hybridization and washing under which nucleotide sequences at least 60% (65%, 70%, preferably 75%) identical to each other typically remain hybridized to each other. Such stringent conditions are known to those skilled in the art and can be found in Current Protocols in Molecular Biology, John Wiley & Sons, N.Y. (1989), 6.3.1-6.3.6. In one embodiment of stringent hybridization conditions are hybridization in 6× sodium chloride/sodium citrate (SSC) at about 45° C., followed by one or more washes in 0.2×SSC, 0.1% SDS at 50-65° C. Preferably, an isolated nucleic acid molecule of the invention that hybridizes under stringent conditions to the coding or non-coding (or "sense" or "anti-sense") sequence that will encode SEQ ID NO's 21 to 32 or their combination, corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein). In addition to naturally-occurring allelic variants of the mutated Activin A type I receptor protein (ACVR1) sequence that may exist in the population, the skilled artisan will further appreciate that changes can be introduced by mutation into the nucleotide sequence encoding mutated Activin A type I receptor protein (ACVR1), thereby leading to changes in the amino acid sequence of the encoded mutated Activin A type I receptor protein (ACVR1), without altering the biological functionality of the encoded mutated Activin A type I receptor protein (ACVR1). Mutations can be introduced by standard techniques, such as site-directed mutagenesis and PCR-mediated mutagenesis. Preferably, conservative amino acid substitutions are made at one or more predicted non-essential amino acid residues.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in Activin A type I receptor protein (ACVR1) is preferably replaced with another amino acid residue from the same side chain family. Alternatively, mutations can be introduced randomly along all or part of an Activin A type I receptor protein (ACVR1) coding sequence, such as by saturation mutagenesis, and the resultant mutants can be screened for biological activity of Activin A type I receptor protein (ACVR1), to identify mutants that retain activity, or in another embodiment, the activity of the mutated Activin A type I receptor protein (ACVR1) as described herein. Following mutagenesis, the encoded protein can be expressed recombinantly and the activity of the protein can be determined.

As defined herein an "isolated" or "substantially pure" nucleic acid (e.g., an RNA, DNA or a mixed polymer) is one which is substantially separated from other cellular components, which naturally accompany a native human sequence or protein, e.g., ribosomes, polymerases, many other human genome sequences and proteins. The term embraces a nucleic acid sequence or protein which has been removed from its naturally occurring environment, and includes recombinant or cloned DNA isolates and chemically synthesized analogs or analogs biologically synthesized by heterologous systems.

A "nucleic acid" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules") in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA" is a DNA that has undergone a molecular biological manipulation.

The phrase "nucleic acid encoding" refers to a nucleic acid molecule which directs the expression of a specific protein or peptide. The nucleic acid sequences include both the DNA strand sequence that is transcribed into RNA and the RNA sequence that is translated into protein. The nucleic acid molecule include both the full length nucleic acid sequences as well as non-full length sequences derived from the full length protein. It being further understood that the sequence includes the degenerate codons of the native sequence or sequences which may be introduced to provide codon preference in a specific host cell.

"Recombinant nucleic acid" is a nucleic acid which is not naturally occurring, or which is made by the artificial combination of two otherwise separated segments of sequence. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions. In one embodiment, the invention provides recombinant DNA constructs that contain ACVR1 cDNA sequences such as wild type ACVR1 or in another embodiment, recombinant DNA constructs comprising ACVR1 cDNA with the mutations described herein.

DNA sequence analysis of all ACVR1 protein-coding exons and splice junctions showed the presence of an identical heterozygous single nucleotide change at cDNA position 617 (c.617G>A) in all examined familial and sporadic FOP patients (FIG. 3b) with classical features of FOP. Investigation of sporadic cases of FOP patients with unambiguous clinical features revealed the presence of the identical de novo mutation in 32 of 32 cases In addition to direct DNA sequence analysis, the G>A nucleotide change can be verified by differential restriction endonuclease digestion (FIG. 4a). In one embodiment, the mutated ACVR1 used in the methods, compositions and kits described herein comprises the amino acid sequence of SEQ ID NO 21. In another embodiment, the mutated ACVR1 used in the methods, compositions and kits described herein comprises the amino acid sequences of SEQ ID NOs 21-32 or combinations thereof.

In one embodiment, the isolated nucleic acid used in the methods, compositions and kits described herein is one wherein the mutation is a c.44C→G mutation, or one wherein the mutation is a c.590-592delCTT mutation, or one wherein the mutation is a c.744G→C mutation, or one wherein the mutation is a c.982G→A mutation, or one wherein the mutation is a c.1124G→C mutation, or one wherein the mutation is a combination thereof. In another embodiment, the mutation results in A156G mutation. In another embodiment, the mutation results in a deletion that replaces Pro197 and Phe 198 with one Leu residue. In another embodiment, the mutation results in R258S mutation. In another embodiment, the mutation results in G328R mutation. In another embodiment, the mutation results in R375P mutation. In another embodiment, the mutation results in a combination of the mutation described herein.

In one embodiment, the isolated nucleic acid used in the methods, compositions and kits described herein is one wherein the mutation is a c617G→A mutation, or a c619C→G mutation, a c982G→T mutation, a c983G→A mutation, a c1067GA mutation, or a combination thereof in other embodiments. In one embodiment, the mutation results in a R206H mutation, or a Q207E mutation, a G328W mutation, a G328E mutation, a G356D mutation, or a combination thereof in other embodiment on the encoded Activin A type I receptor protein (ACVR1). In one embodiment, the Activin A type I receptor protein (ACVR1) used in the methods, compositions and kits described herein is encoded from an isolated nucleic acid that is a compilation of any one of SEQ ID NOs. 21-32, carrying at least one mutation, or all the mutations, without any other changes to the nucleic acid sequences other than the mutations described herein.

In one embodiment, the human wild-type ACVR1 protein has the following amino acid sequence:

```
                                         (SEQ ID NO. 26)
MVDGVMILPVLIMIALPSPSMEDEKPKVNPKLYMCVCEGLSCGNEDHC

EGQQCFSSLSINDGFHVYQKGCFQVYEQGKMTCKTPPSPGQAVECCQG

DWCNRNITAQLPTKGKSFPGTQNFHLEVGLIILSVVFAVCLLACLLGV

ALRKFKRRNQERLNPRDVEYGTIEGLITTNVGDSTLADLLDHSCTSGS

GSGLPFLVQRTVARQITLLECVGKGRYGEVWRGSWQGENVAVKIFSSR

DEKSWFRETELYNTVMLRHENILGFIASDMTSRHSSTQLWLITHYHEM

GSLYDYLQLTTLDTVSCLRIVLSIASGLAHLHIEIFGTQGKPAIAHRD

LKSKNILVKKNGQCCIADLGLAVMHSQSTNQLDVGNNPRVGTKRYMAP

EVLDETIQVDCFDSYKRVDIWAFGLVLWEVARRMVSNGIVEDYKPPFY

DVVPNDPSFEDMRKVVCVDQQRPNIPNRWFSDPTLTSLAKLMKECWYQ

NPSARLTALRIKKTLTKIDNSLDKLKTDC.
```

The human wild-type ACVR1 coding sequence is set forth in SEQ ID NO: 50 (See GenBank Accession# NM_001105.2).

```
                                         (SEQ ID NO: 50)
atggtagatggagtgatgattcttcctgtgcttatcatgattgctctc ccctcccctagtatggaagatgagaagcccaaggtcaacccaaactc tacatgtgtgtgtgtgaaggtctctcctgcggtaatgaggaccactgt gaaggccagcagtgcttttcctcactgagcatcaacgatggcttccac gtctaccagaaaggctgcttccaggtttatgagcagggaaagatgacc tgtaagacccccgccgtccctggccaagctgtggagtgctgccaaggg gactggtgtaacaggaacatcacggcccagctgcccactaaaggaaaa tccttccctggaacacagaatttccacttggaggttggcctcattatt ctctctgtagtgttcgcagtatgtcttttagcctgcctgctgggagtt gctctccgaaaatttaaaaggcgcaaccaagaacgcctcaatccccga gacgtggagtatggcactatcgaagggctcatcaccaccaatgttgga gacagcactttagcagatttattggatcattcgtgtacatcaggaagt ggctctggtcttccttttctggtacaaagaacagtggctcgccagatt acactgttggagtgtgtcgggaaaggcaggtatggtgaggtgtggagg ggcagctggcaaggggaaaatgttgccgtgaagatcttctcctcccgt gatgagaagtcatggttcagggaaacggaattgtacaacactgtgatg ctgaggcatgaaaatatcttaggtttcattgcttcagacatgacatca agacactccagtacccagctgtggttaattacacattatcatgaaatg ggatcgttgtacgactatcttcagcttactactctggatacagttagc tgccttcgaatagtgctgtccatagctagtggtcttgcacatttgcac atagagatatttgggacccaagggaaaccagccattgcccatcgagat ttaaagagcaaaaatattctggttaagaagaatggacagtgttgcata gcagatttgggcctggcagtcatgcattcccagagcaccaatcagctt
```

-continued

```
gatgtggggaacaatccccgtgtgggcaccaagcgctacatggccccc gaagttctagatgaaaccatccaggtggattgtttcgattcttataaa agggtcgatatttgggcctttggacttgttttgtgggaagtggccagg cggatggtgagcaatggtatagtggaggattacaagccaccgttctac gatgtggttcccaatgacccaagttttgaagatatgaggaaggtagtc tgtgtggatcaacaaaggccaaacatacccaacagatggttctcagac ccgacattaacctctctggccaagctaatgaaagaatgctggtatcaa aatccatccgcaagactcacagcactgcgtatcaaaaagactttgacc aaaattgataattccctcgacaaattgaaaactgactgttga.
```

The ACVR1 c.617G>A mutation causes an amino acid change in codon 206 (R206H; CGC>CAC). Amino acid 206 is highly conserved among vertebrates (FIG. 3b), and is also highly conserved among human ACVR1 family members (FIG. 6). Codon 206 is at the end of the highly conserved glycine/serine (GS) activation domain at the junction of the protein kinase domain (FIG. 3a). Activation of a BMP/TGFβ type I receptor serine-threonine kinase, and consequent signaling, requires phosphorylation at the GS domain by a BMP type II receptor.

Figure 5:
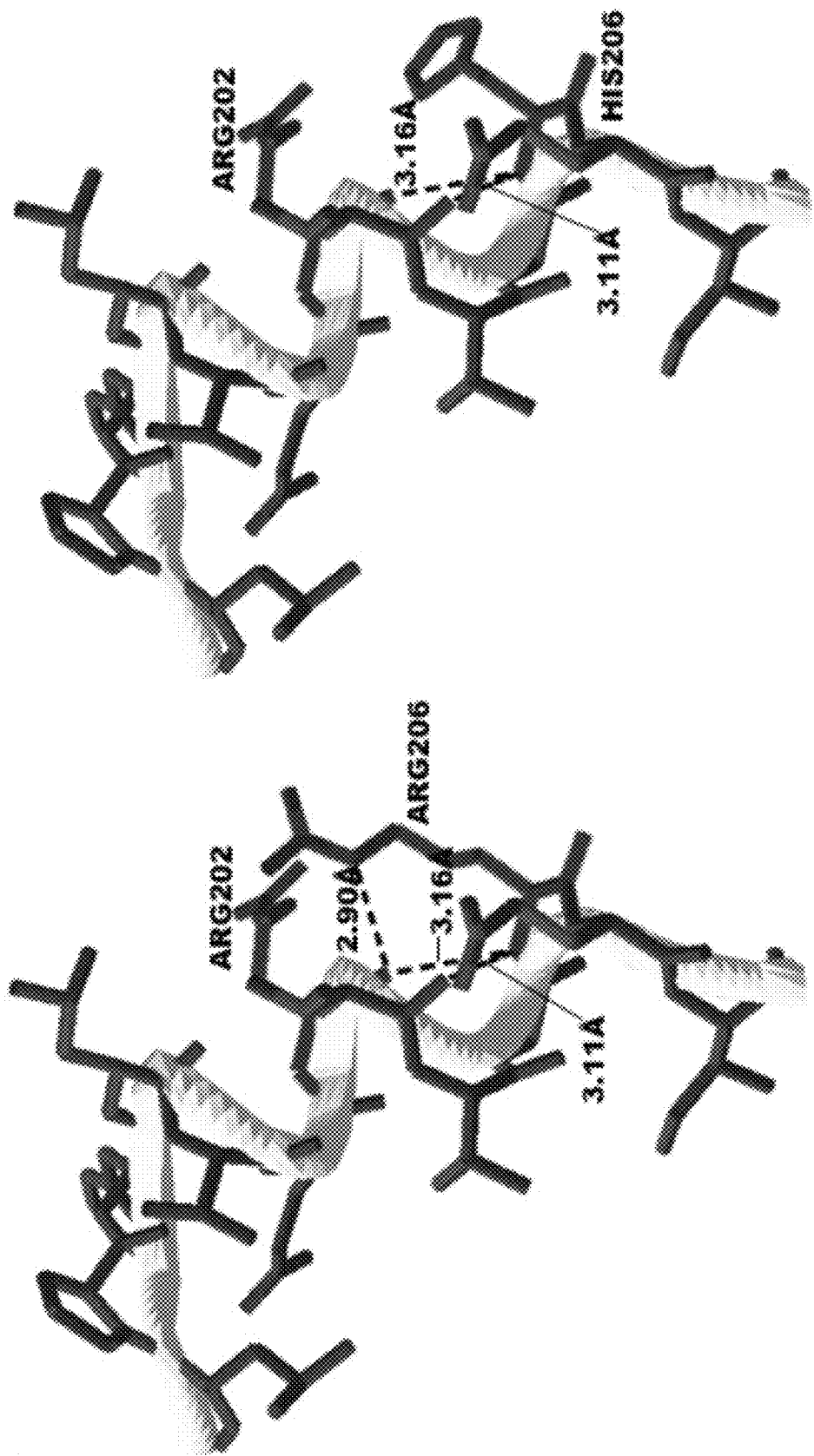
FIG. 5 shows the effect of the Arg206His mutation on the predicted protein structure of the ACVR1 α-helix, residues 198-206. Homology model of wild-type ACVR1 (at left) shows that the most likely conformation (lowest scoring rotamer) of the arginine 206 side chain predicts that it interacts with the α-helix backbone to stabilize the protein. Homology model of mutant Arg206His ACVR1 (at right) shows that the most likely conformation (lowest scoring rotamer) of the histidine 206 side chain does not interact with the α-helix backbone which is predicted to result in partial destabilization of the protein.

PredictProtein and CPHmodels both predict a partial destabilization of the α-helix formed by ACVR1 amino acids 198-206 (FIG. 5). The R206H mutation forms a shorter side chain that alters the electrostatic potential compared to the wild type ACVR1 protein (SEQ ID NO. 26), disrupting intramolecular interactions that stabilize the ACVR1 or altering interactions between the GS domain and other signaling pathway molecules.

The GS domain is a critical site for binding and activation of R-Smad signaling proteins and is a binding site of FKBP12, an inhibitory protein that prevents leaky activation of the type I receptor in the absence of ligand. FKBP12 interactions with the GS domain may be altered, leading to promiscuous activity of ACVR1. Without wishing to be bound by theory, R206H mutations in ACVR1 specifically perturb BMP signaling in FOP involves dysregulation of BMP receptor oligomerization, or internalization, and/or activation of downstream signaling.

In one embodiment, the isolated nucleic acid described herein, which is used in the compositions, methods and kits described herein, is DNA, or RNA, cDNA, genomic DNA, or a PCR product or their combination in other embodiments. In one embodiment, the DNA, or RNA, cDNA, genomic DNA, or a PCR product or their combination as described herein, are detectibly labeled. In another embodiment, the DNA, or RNA, cDNA, genomic DNA, or a PCR product or their combination as described herein, are detectibly labeled with a label that is a radioactive label, or colorimetric, luminescent, fluorescent marker, or gold label in other embodiments.

In one embodiment, the isolated nucleic and amino acids described hereinabove are capable of being hybridized to by the oligonucleotides described herein, wherein the hybridized oligonucleotides are used in the compositions, methods and kits described herein. In one embodiment, the described herein is an oligonucleotide capable of hybridizing to any embodiment of a nucleotide described hereinabove.

In one embodiment, the invention provides an oligonucleotide of at least 15 nucleotides capable of specifically hybridizing with a sequence of the nucleic acid which encodes the mutated Activin A type I receptor protein (ACVR1), wherein the nucleic acid enhances activity of bone morphogenetic protein (BMP) receptor or bone morphogenetic protein (BMP) receptor signaling; and is pathognomonic of Fibrodysplasia Ossificans Progressiva (FOP) and comprises the sequence as set forth in SEQ ID NOs. 21-25 or variants thereof.

In one embodiment, the oligonucleotides described herein, which are capable of specifically hybridizing with a sequence of the nucleic acid which encodes the mutated Activin A type I receptor protein (ACVR1), as described herein, that is used in the compositions, methods and kits described herein, is DNA, or RNA, cDNA, genomic DNA, or a PCR product or their combination in other embodiments. In one embodiment, the DNA, or RNA, cDNA, genomic DNA, or a PCR product or their combination as described herein, are detectibly labeled. In another embodiment, the DNA, or RNA, cDNA, genomic DNA, or a PCR product or their combination as described herein, are detectibly labeled with a label that is a radioactive label, or colorimetric, luminescent, fluorescent marker, or gold label in other embodiments.

In one embodiment, provided herein is a nucleic acid having a sequence complementary to the sequence of the isolated nucleic acid encoding a mutated Activin A type I receptor protein (ACVR1), wherein the nucleic acid enhances activity of bone morphogenetic protein (BMP) receptor and/or signaling and is pathognomonic of Fibrodysplasia Ossificans Progressiva (FOP).

In one embodiment, the isolated nucleic or amino acid sequences described hereinabove, are used in the compositions described herein.

According to this aspect of the invention and in one embodiment, the invention provides molecular beacon comprising: an oligonucleotide comprising a stem and a loop structure and having a photoluminescent dye at one of the 5' or 3' ends and a quenching agent at the opposite 3' or 5' ends, wherein said loop consists of about 8-25 bases, substantially complimentary to the nucleotide sequence encoding SEQ ID NOs 21-32 or their combination. in another embodiment, the invention provides molecular beacon comprising: an oligonucleotide comprising a stem and a loop structure and having a photoluminescent dye at one of the 5' or 3' ends and a quenching agent at the opposite 3' or 5' ends, wherein said loop consists of about 8-25 bases, substantially complimentary to a nucleotide sequence comprising a combination of any mutation described herein. In another embodiment, the mutated Activin A type I receptor protein (ACVR1) has a R206H mutation, a Q207E mutation, a G328W mutation, a G328E mutation, a G356D mutation, or a combination thereof.

In some embodiments, a nucleic acid described herein exhibits substantial complimentarity to its target sequence, which may be a nucleic acid encoding a protein, such as mutated ACVR1 protein. As used herein, "complementary" indicates that the oligonucleotide has a base sequence containing an at least 15 contiguous base region that is at least 70% complementary, or preferably at least 80% complementary, or more preferably at least 90% complementary, or even 100% complementary to an-at least 15 contiguous base region present in a target gene sequence (excluding RNA and DNA equivalents). (Those skilled in the art will readily appreciate modifications that could be made to the hybridization assay conditions at various percentages of complementarity to permit hybridization of the oligonucleotide to the target sequence while preventing unacceptable levels of non-specific hybridization.). The degree of complementarity is determined by comparing the order of nucleobases making up the two sequences and does not take into consideration other structural differences which may exist between the two sequences, provided the structural differences do not prevent hydrogen bonding with complementary bases. The degree of complementarity between two sequences can also be expressed in terms of the number of base mismatches present in each set of at least 15 contiguous bases being compared, which may range from 0-3 base mismatches, so long as their functionality for the purpose used is not compromised.

"Sufficiently complementary" refers to a contiguous nucleic acid base sequence that is capable of hybridizing to another base sequence by hydrogen bonding between a series of complementary bases. Complementary base sequences may be complementary at each position in the base sequence of an oligonucleotide using standard base pairing (e.g., G:C, A:T or A:U pairing) or may contain one or more residues that are not complementary using standard hydrogen bonding (including abasic "nucleotides"), but in which the entire complementary base sequence is capable of specifically hybridizing with another base sequence under appropriate hybridization conditions. Contiguous bases are generally at least about 80%, or at least about 90%, or about 100% complementary to a sequence to which an oligonucleotide is intended to specifically hybridize. Appropriate hybridization conditions are well known to those skilled in the art, can be predicted readily based on base sequence composition, or can be determined empirically by using routine testing (e.g., See Sambrook et al., Molecular Cloning. A Laboratory Manual, $2^{nd}$ ed. (Cold Spring Harbor Laboratory Press, Cold Spring Harbor, N.Y., 1989).

In one embodiment, the isolated nucleic acids and their encoded amino acid, or the embodiments of compositions described hereinabove or their combination, are used in the methods and kits described herein.

Any of the mutations described herein resulting in a mutated Activin A type I receptor (ACVR1), may affect the Activin A type I receptor (ACVR1) to enhances activity or signaling of bone morphogenetic protein (BMP). Thus, it will be appreciated that a combination of mutations on ACVR1 will creates a different degree of activity or signaling of BMP.

In one embodiment, the invention provides a method of treating Fibrodysplasia Ossificans Progressiva (FOP) in a subject, comprising the step of administering to said subject a siRNA specific against a nucleic acid encoding a mutated Activin A type I receptor (ACVR1) gene relative to a wild-type Activin A type I receptor protein (ACVR1) as set forth in SEQ ID NO. 26.

The term "siRNA" refers to RNA interference, which refers to the process of sequence-specific post-transcriptional gene silencing in animals, mediated by short interfering RNAs (siRNAs). Without wishing to be bound by theory, the process of post-transcriptional gene silencing is an evolutionarily-conserved cellular defense mechanism used to prevent the expression of foreign genes. Such protection from foreign gene expression evolved in response to the production of double-stranded RNAs (dsRNAs) derived from viral infection from the random integration of transposon elements into a host genome via a cellular response that specifically destroys homologous single-stranded RNA of viral genomic RNA. As discussed below, the presence of dsRNA in cells triggers the RNAi response.

The presence of long dsRNAs in cells stimulates the activity of a ribonuclease III enzyme referred to as dicer. Dicer is involved in the processing of the dsRNA into short pieces of dsRNA known as short interfering RNAs (siRNAs). Short interfering RNAs, such as those derived from dicer activity, are about 21 to about 23 nucleotides in length and comprise about 19 base pair duplexes. Small RNAs function by base-pairing to complementary RNA or DNA target sequences. When bound to RNA, small RNAs trigger RNA cleavage or translational inhibition of the target sequence. When bound to DNA target sequences, small interfering RNAs mediate DNA methylation of the target sequence. The consequence of these events is the inhibition of gene expression, which in embodiment of the present invention is a gene encoding a mutated ACVR1 protein described herein.

In one embodiment, the siRNA of a mutated ACVR1 gene exhibits substantial complimentarity to its target sequence. As used herein, "substantial complementarity" indicates that the oligonucleotide has a base sequence containing an at least 15 contiguous base region that is at least 70% complementary, or preferably at least 80% complementary, or more preferably at least 90% complementary, or up to 100% complementary to an at least 15 contiguous base region present of a target gene sequence (excluding RNA and DNA equivalents). Those skilled in the art will readily appreciate modifications that could be made to the hybridization assay conditions at various percentages of complementarity to permit hybridization of the oligonucleotide to the target sequence while preventing unacceptable levels of non-specific hybridization. The degree of complementarity is determined by comparing the order of nucleobases making up the two sequences and does not take into consideration other structural differences which may exist between the two sequences, provided the structural differences do not prevent hydrogen bonding with complementary bases. The degree of complementarity between two sequences can also be expressed in terms of the number of base mismatches present in each set of at least 15 contiguous bases being compared, which may range from 0-3 base mismatches, so long as their functionality for the purpose used is not compromised.

In one embodiment, the siRNA of a mutated ACVR1 gene, is sufficiently complimentary to its target sequence. As used herein, "sufficiently complementary" refers to a contiguous nucleic acid base sequence that is capable of hybridizing to another base sequence by hydrogen bonding between a series of complementary bases. In another embodiment, complementary base sequences may be complementary at each position in the base sequence of an oligonucleotide using standard base pairing (e.g., G:C, A:T or A:U pairing) or may contain one or more residues that are not complementary using standard hydrogen bonding (including abasic "nucleotides"), but in which the entire complementary base sequence is capable of specifically hybridizing with another base sequence under appropriate hybridization conditions. Contiguous bases are at least about 80%, or at least about 90%, or about 100% complementary to a sequence to which an oligonucleotide is intended to specifically hybridize in another embodiment. Appropriate hybridization conditions are well known to those skilled in the art, can be predicted readily based on base sequence composition, or can be determined empirically by using routine testing (e.g., See Sambrook et al., Molecular Cloning. A Laboratory Manual, $2^{nd}$ ed. (Cold Spring Harbor Laboratory Press, Cold Spring Harbor, N.Y., 1989).

The term "nucleic acid" as used in connection with siRNA, refers to a polymer or oligomer composed of nucleotide units (ribonucleotides, deoxyribonucleotides or related structural variants or synthetic analogs thereof) linked via phosphodiester bonds (or related structural variants or synthetic analogs thereof). Thus, the term refers to a nucleotide polymer in which the nucleotides and the linkages between them are naturally occurring (DNA or RNA), as well as various analogs, for example and without limitation, peptide-nucleic acids (PNAs), phosphoramidates, phosphorothioates, methyl phosphonates, 2'-O-methyl ribonucleic acids, and the like.

The term "treatment" refers to any process, action, application, therapy, or the like, wherein a subject, including a human being, is subjected to medical aid with the object of improving the subject's condition, directly or indirectly. The term "treating" refers to reducing incidence, or alleviating symptoms, eliminating recurrence, preventing recurrence, preventing incidence, inhibiting, delaying onset, improving symptoms, improving prognosis or a combination thereof. "Treating" embraces the amelioration of an existing condition. The skilled artisan will understand that treatment does not necessarily result in the complete absence or removal of symptoms. Treatment also embraces palliative effects: that is, those that reduce the likelihood of a subsequent medical condition. The alleviation of a condition that results in a more serious condition is encompassed by this term.

In one embodiment, the methods of the invention are used in combination with other therapeutic agents, such as, but not limited to bisphosphonates, which inhibits osteoclastic-mediated bone resorption. In another embodiment, the other therapeutic agent is Etidronate, which may be delivered to a subject in need thereof operably linked to an antibody, a fragment thereof or their combination.

In one embodiment, the invention provides a method of treating a pathology associated with heterotopic ossification in a subject, comprising the step of administering to said subject an therapeutically effective amount of siRNA against a nucleic acid encoding a mutated Activin A type I receptor (ACVR1), wherein the Activin A type I receptor (ACVR1) enhances activity or signaling of bone morphogenetic protein (BMP). In another embodiment, the pathology associated with heterotopic ossification is ossification resulting from hip replacement surgery, or valvular heart disease, closed head trauma, spinal cord injuries, sports injuries, blast injuries, or a combination thereof.

In one embodiment, enhancing activity or signaling of morphogens provided herein stimulate the proliferation, growth and differentiation of osteoblasts in vitro and in another embodiment, can induce bone formation in osteoporotic bone tissue in vivo when provided systemically to a mammal, or directly to bone tissue, without an associated matrix carrier. In one embodiment, enhancing activity or signaling of the morphogens inhibit multinucleation of activated early mononuclear phagocytic cells.

The bone morphogenetic proteins (BMPs) are a group of activin proteins that in one embodiment, induce de novo cartilage and bone formation, and appear to be essential for skeletal development during mammalian embryogenesis (Wang, Trends Biotechnol. 11, 379, 1993). Due to their osteoinductive properties the BMPs are of clinical interest. In one embodiment, early in the process of fracture healing the concentration of bone morphogenetic protein-4 (BMP-4) increases dramatically. In another embodiment upregulation of BMP-4 transcription promotes bone healing in mammals. In another embodiment, enhancing activity or signaling of BMP may play an important role in bone remodeling and fracture repair, which in another embodiment, may be achieved by the methods described herein.

In one embodiment, the treatment methods described herein further comprise administering to the subject a signal transduction inhibitor or various signal transduction inhibitors designed or selected specifically to block the activity of the various mutated ACVR1 proteins or, in another embodiment, leave the unmutated wild ACVR1 molecules unimpaired to carry-out their normal function. In one embodiment the signal transduction inhibitor is administered in combination with the siRNA specific against the mutated ACVR1 described herein.

Inhibins are endogenous antagonists of activin signaling. Inhibin B and inhibin A are heterodimeric proteins in the TGF-β superfamily composed of αβB or αβA subunits, respectively. Inhibins are recognized as regulators of reproduction that antagonistically modulate the endocrine interaction of the pituitary and gonadal systems, which are produced by the gonads in response to FSH and act at the pituitary to attenuate activin effects such as BMPs. Activins, like BMPs, stimulate target cells by assembling receptor complexes containing type I receptors such as ACVR1 at the cell membrane. In these ligand-receptor complexes, distinct activin-specific type I receptors are activated and in turn activate activin-specific Smads. Inhibins are used in the combination therapy according to the treatment embodiments described herein, as a signal transduction antagonist.

Follistatin is a natural antagonist that binds activin with high affinity and neutralizes its biological activities by preventing activin interaction with its membrane receptors. Follistatin is a single-chain glycoprotein of 35 kDa which is composed of four cysteine-rich domains, three of which are homologous and highly conserved. Follistatin and other follistatin-related molecules act by regulating the availability of TGF-β-related or other growth factors, thereby influencing cellular migration, proliferation, and differentiation.

Antagonists of BMP signal transduction activity include fetuin glycoprotein, also known as α2-HS glycoprotein in humans, and the DAN family of BMP antagonists, such as noggin, chordin, follistatin, and gremlin. Noggin, or chordin, follistatin, gremlin or their combination are administered in the methods of treating FOP, or other heterotopic ossification pathgologies described herein. Gremlin regulates outgrowth, chondrogenesis and programmed cell death in the developing limb or regulation of the onset of neural crest migration by coordinated activity of BMP4 and noggin in the dorsal neural tubeFetuin blocks osteogenesis, or ossification and is used in inhibiting signal transduction as described herein. Noggin binds several BMPs with very high (picomolar) affinities, with a marked preference for BMP2 and BMP4. By binding tightly to BMPs, Noggin prevents BMPs from binding their receptors, thereby acting as a signal transduction inhibitor. Chordin also antagonizes BMP signaling by directly binding BMP proteins, thereby preventing receptor activation, such as an ACVR1 receptor or a mutated ACVR1.

In one embodiment, the kits described herein, use the compositions described herein and may be used to carry out the methods described herein.

As used herein, "subject" refers to a human or any other animal which contains a mutated ACVR1 that. A subject can be a patient, which refers to a human presenting to a medical provider for diagnosis or treatment of a disease. A human includes pre and post natal forms.

The term "about" as used herein means in quantitative terms plus or minus 5%, plus or minus 10%, or in another embodiment plus or minus 15%, or in another embodiment plus or minus 20%.

All sequence citations, accession numbers, references, patents, patent applications, scientific publications or other documents cited are hereby incorporated by reference.

The following examples are presented in order to more fully illustrate the preferred embodiments of the invention. They should in no way be construed, however, as limiting the broad scope of the invention.

EXAMPLES

Example 1

A Mutation in the BMP Type I Receptor ACVR1 Causes Inherited and Sporadic Fibrodysplasia Ossificans Progressiva

Materials and Methods
Subjects and Clinical Evaluation

Blood samples were obtained following informed consent from individuals and/or their parents in accordance with a protocol approved by the Institutional Review Board of the University of Pennsylvania School of Medicine.

Linkage Studies

Genomic DNA was isolated directly from blood samples, buccal swabs, or from lymphoblast cell lines (LCLs) using QIAamp DNA Blood reagents (Qiagen) and standard protocols. EBV-transformed LCLs were established by standard protocols. Some samples were whole genome-amplified using Repli-G reagents (Molecular Staging Inc.) and standard protocols. Genome wide linkage analysis was carried out through the University of Utah School of Medicine Genomics Core Facility using an ABI 3130xl Genetic Analyzer and scoring with ABI GeneMapper v.3. All families were genotyped using 400 microsatellite markers from the ABI Prism linkage mapping set v.2.5 (medium density 10 cM set). For fine mapping, markers selected from the Marshfield genetic map were used. Family A genotyping data from an earlier study was integrated into this analysis. Genehunter v.2 software was used to calculate multipoint parametric LOD scores. A model of an autosomal dominant trait with 100% penetrance of the FOP gene was assumed, with a population prevalence of FOP of 1 per million. SNP genotyping was conducted through the University of Pennsylvania School of Medicine Microarray Core Facility using the Affymetrix GeneChip Mapping 10K Array and Genespring GT software (Agilent Technologies)

Mutation Analysis

Mutations in ACVR1 were screened for by PCR-amplification of genomic DNA from blood or LCLs corresponding to the 9 exons containing protein coding sequences (ACVR1 Transcript Report, Ensembl v35), using exon-flanking primers (see Table 1 for primer sequences). DNA sequence analysis of genomic DNA was carried out on an ABI3730 sequencer through the University of Pennsylvania School of Medicine DNA Sequencing Facility. Sequence data were analyzed using 4Peaks software v.1.6 (http://www.mekentosj.com/4peaks/).

TABLE 1

ACVR1 primers for genomic DNA PCR amplification.

| Protein coding exon # | Forward primer | Reverse primer | PCR product size |
|---|---|---|---|
| Exon 1 | 5'-GGCAGTTTGAAGGTGGTATG-3' (SEQ ID NO. 1) | 5'-ACCCAAAAAGATGTGAGTCAC-3' (SEQ ID NO. 11) | 184 bp |
| Exon 2 | 5'-ATATGAACACCACAGGGGG-3' (SEQ ID NO. 2) | 5'-CCTTTCTGGTAGACGTGGAAG-3' (SEQ ID NO. 12) | 449 bp |
|  | 5'-TTTTTTCCCCTTCCTTTCTCTC-3' (SEQ ID NO. 3) | 5'-CAGGGTGACCTTCCTTGTAG-3' (SEQ ID NO. 13) | 438 bp |
| Exon 3 | 5'-AATTCCCCTTTTCCCTCCAAC-3' (SEQ ID NO. 4) | 5'-TAAGAACGTGTCTCCAGACACC-3' (SEQ ID NO. 14) | 300 bp |
| Exon 4 | 5'-CCAGTCCTTCTTCCTTCTTCC-3' (SEQ ID NO. 5) | 5'-AGCAGATTTTCCAAGTTCCATC-3' (SEQ ID NO. 15) | 350 bp |
| Exon 5 | 5'-TCCCAAGCTGAGTTTCTCC-3' (SEQ ID NO. 6) | 5'-AGAGCAAAGGCAGACAATTG-3' (SEQ ID NO. 16) | 346 bp |
| Exon 6 | 5'-GACATTTACTGTGTAGGTCGC-3' (SEQ ID NO. 7) | 5'-AGAGATGCAACTCACCTAACC-3' (SEQ ID NO. 17) | 438 bp |
| Exon 7 | 5'-TGGGGTTGGTTTAAAATCCTTC-3' (SEQ ID NO. 8) | 5'-AGGTAGCTGGATCAAGAGAAC-3' (SEQ ID NO. 18) | 337 bp |
| Exon 8 | 5'-CACATTATAACCTGTGACACCC-3' (SEQ ID NO. 9) | 5'-ATACCAGTTGAAACTCAAAGGG-3' (SEQ ID NO. 19) | 299 bp |
| Exon 9 | 5'-GTATTGCTGCTTTTGGCAC-3' (SEQ ID NO. 10) | 5'-CAGTCCCTACCTTTGCAAC-3' (SEQ ID NO. 20) | 700 bp |

Protein coding exon 1 contains the ATG protein start codon. The R206H mutation is in protein coding exon 4.

Differences in restriction endonuclease recognition sites were identified using MacVector v.7.2 software (ABI). We amplified 0.1 ug of genomic DNA using primers for protein coding exon 4. Following agarose gel electrophoresis, the PCR products (350 bp) were recovered from agarose using QIAquick Gel Extraction reagents (Qiagen). Purified PCR product was digested with either HphI (5 U/ul) or Cac8I (4 U/ul) (both from New England Biolabs) at 37° C. for 2 hours. Fragments were resolved on 3% NuSieve 3:1 agarose (FMC BioProducts) gels with 100 bp ladder (New England Biolabs) as size markers.

Cell Culture and RNA Analysis

LCLs from 4 FOP patients and 4 controls were grown in RPMI 1640 media with 15% FBS. Total RNA was extracted from $10^7$ cells using RNeasy reagents (Qiagen) and performed reverse transcription using SuperScript III (Invitrogen). PCR was used amplify the region corresponding to protein coding exon 4 with specific primers (see Table 1 for primer sequences) and Taq DNA polymerase (Invitrogen) then directly sequenced the amplified cDNA as described above.

Molecular Modeling of Protein Structure

Structural protein homology modeling was based on the PDB structure for type I TGFβ receptor kinase which is 66% identical to ACVR1 residues 178-498. This region includes the serine/threonine protein kinase catalytic domain and the GS motif with arginine residues at ACVR1 positions 202 and 206. ACVR1 amino acid 178-498 sequence was submitted to PredictProtein (http://www.embl-heidelberg.de/predictprotein/submit_def.html), CPHmodels homology-modeling server (http://www.cbs.dtu.dk/services/CPHmodels/) and the SWISS-MODEL homology-modeling server (http://swiss-model.expasy.org/). Visualization used the DeepView Swiss PDB Viewer.

Gene and Protein Analysis

Genes in the linked region were identified through the National Center for Biotechnology Information Entrez Map Viewer and the UCSC Genome Browser. The intron-exon boundaries of the ACVR1 gene were obtained through GenBank, Ensembl Human Genome Server, and the University of Santa Cruz. Genomic DNA positions of markers and the ACVR1 gene are from the UCSC Genome Browser (May 2004, Build 35). Transcript and exon information is from Ensembl (Gene ID ENSG00000115170; transcript ID ENST00000263640) which reports 11 exons for ACVR1 (exons 1 and 2 contain only 5'UTR; the protein start site is in exon 3), consistent with GenBank BC033867, full length cDNA clone). All databases are consistent for the sequence information for the 9 exons containing protein-coding sequences, however, additional/alternate exons containing 5'UTRs are reported. ACVR1 protein ID is Q04771 (Pfam, SWIS-SPROT). Clustal W (with the MacVector v 7.2 software program) was used for multiple protein alignment using sequences from GenBank.

Genbank Accession Numbers

ACVR1 cDNA, NM_001105; ACVR1 coding region, NT_005403. ACVR1 protein for *Homo sapiens* (human), NP_001096; *Mus musculus* (mouse), NP_031420; *Rattus norvegicus* (rat), NP_077812; *Canis familiaris* (dog), XP_856152; *Bos taurus* (cow), NP_788836; *Gallus gallus* (chick), NP_989891; *Xenopus laevis* (frog), AAH88947; *Danio rerio* (zebrafish), NP_571420. *Fugu rubripes* (pufferfish) sequence was from Ensembl prediction SINFRUG00000134562.

Results

The formation of bone where it is neither needed nor wanted can lead to devastating consequences. FOP (OMIM 135100) is the most severe and disabling disorder of extra-skeletal (heterotopic) ossification in humans. Heterotopic ossification in FOP begins in childhood and can be induced by trauma, or may occur without warning. Bone formation is episodic and progressive, leading to extra-articular ankylosis of all major joints of the axial and appendicular skeleton, rendering movement impossible (FIG. 1a)

The severe disability of FOP results in low reproductive fitness and few examples of inheritance are known. When observed, genetic transmission is autosomal dominant and can be inherited from either mothers or fathers. With the identification of additional pedigrees, a more conservative genome-wide linkage analysis was conducted using a subset of five families with the most stringent and unambiguous features of FOP (congenital malformation of the great toes and progressive heterotopic ossification in characteristic anatomic patterns; FIG. 1a, b) in all affected family members.

Characteristic Clinical Features of FOP

FOP is the most severe and disabling disorder of extra-skeletal (heterotopic) ossification in humans. Heterotopic ossification in FOP begins in childhood and can be induced by trauma, or may occur without warning. Bone formation is episodic, progressive, and extensive, leading to the extra-articular ankylosis of all the major joints of the axial and appendicular skeleton, rendering movement impossible (FIG. 1a). Flareups of FOP arise and progress in a well-defined spatial pattern that result in ribbons, sheets, and plates of bone that fuse the joints of the axial and appendicular skeleton, entombing the patient in a "second skeleton" of heterotopic bone. One of the more readily recognized skeletal malformations in FOP patients are great toe malformations of metatarsals and proximal phalanges that can occur along with microdactyl), fused interphalangeal joints, and hallux valgus deviations at the metatarsophalangeal joints (FIG. 1b). The severe disability of FOP results in low reproductive fitness and few examples of inheritance of FOP are known. Death often results by the fifth decade from thoracic insufficiency syndrome. There is no effective prevention or treatment.

Descriptions of FOP Families.

Figure 2B:
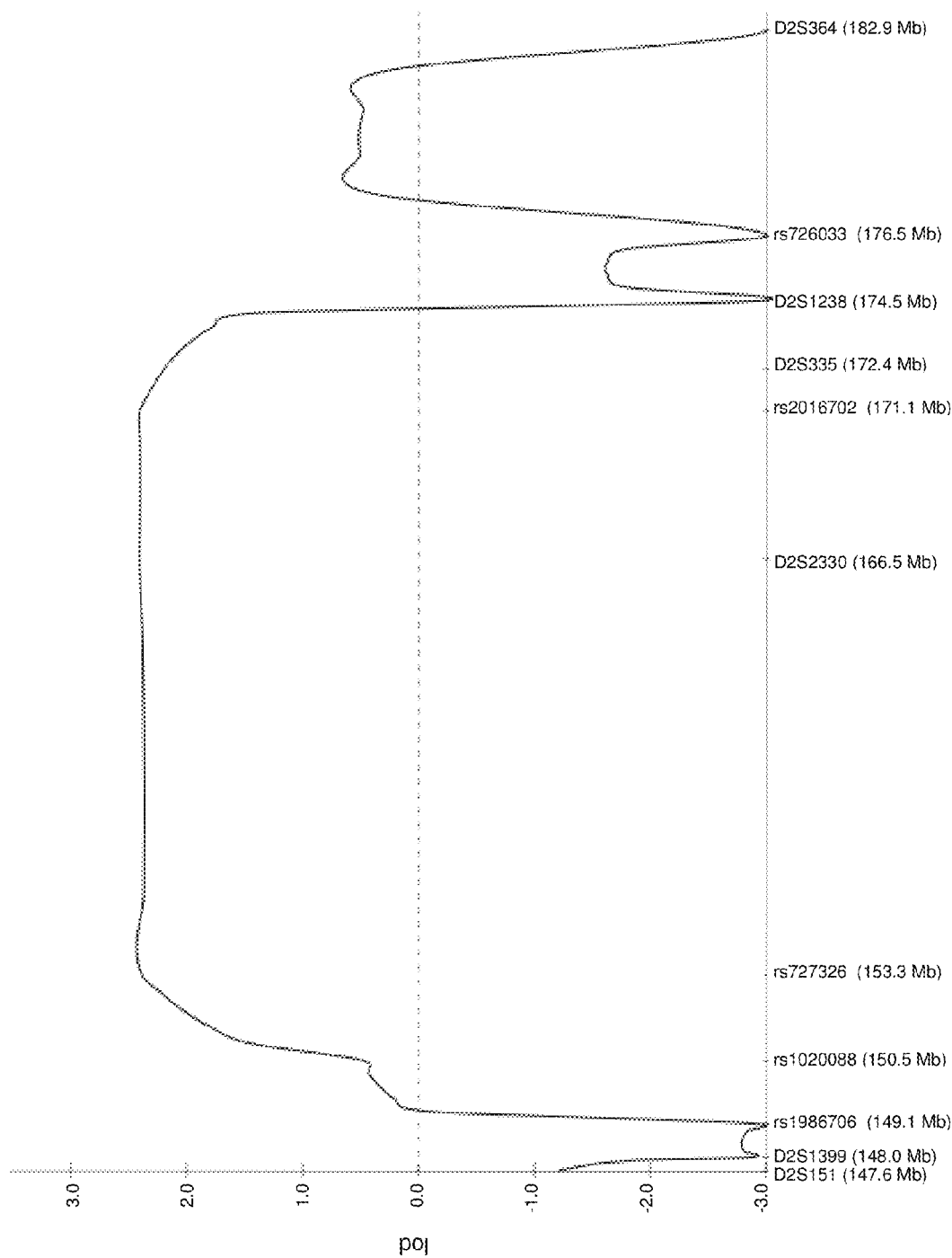

The initial linkage analysis used four families that showed autosomal dominant inheritance of FOP-type heterotopic ossification, although not all affected individuals in each pedigree had characteristic malformation of the great toes. With the experience of examining more patients over time, concern was raised as to whether patients without both of these features could confound linkage analysis due to locus heterogeneity or mosaicism. This clinical information prompted the decision to use only a subset of families in whom all affected individuals had unambiguous features of malformed toes and progressive heterotopic ossification (FIG. 1a, b) in the present linkage analysis (FIG. 2a). A combined multipoint lod plot for the markers in the chromosome 2 FOP linkage region is shown in FIG. 2b.

Investigation of the ACVR1 c.617G>A (R206H) mutation in the five families used in the current linkage analysis show that all affected members have the mutation and none of the unaffected members available for examination carry the mutation. Of the four families used in the initial linkage study, Family 1 had unambiguous features of FOP in all affected individuals and was used in the current study (Family A in FIG. 2a). (Family numbers are those used in Feldman, G. et al. Fibrodysplasia ossificans progressiva, a heritable disorder of severe heterotopic ossification, maps to human chromosome 4q27-31. *Am. J. Hum. Genet.* 66, 128-135 (2000), which is hereby incorporated herein in its entirety; letters are used to identify families in the current study.) Family 2 showed ambiguous FOP features, with one member possessing only toe malformations without heterotopic ossification, while another had no toe malformation and mild heterotopic ossification that has not progressed. This family was not used in the current linkage analysis since every member did not fulfill the most stringent diagnostic criteria for FOP. No ACVR1 c.617G>A mutation was detected in any member of this family. In Family 3, FOP was inherited from mother to children and all had classic features of FOP. However, this family was not available for confirmational re-examination and was thus excluded from the current linkage analysis. Subsequent evaluation of Family 3 with chromosome 2 markers confirmed linkage to the FOP locus and all affected members of this family contain the ACVR1 c.617G>A mutation. Family 4 had two affected members, one with classic features of FOP (daughter), while the other (father) showed only mild evidence of heterotopic ossification with no toe malformation. The daughter was heterozygous for ACVR1 c.617G>A, while the father does not carry a germline mutation.

An additional very recently identified family consists of a father with FOP (deceased, unavailable for analysis), an unaffected mother, and two affected children with classic FOP features. This family shows linkage to the chromosome 2 FOP locus and both children are heterozygous for ACVR1 c.617G>A on the paternally inherited allele.

c.617G>A (R206H) Mutations in the ACVR1 Gene in Patients with FOP

The chromosome 2q FOP critical genomic region (FIG. 3a) spans ~23.9 Mb between markers rs1020088 (centromeric) at 150,654,341 bp and D2S1238 (telomeric) at 174,505,230 bp as annotated by UCSC GenomeBrowser. The ACVR1 gene spans ~138.6 kb of genomic DNA (chromosome 2: 158,418,469-158,557,131). ACVR1 encodes a 509 amino acid protein that contains a ligand binding region, a transmembrane (TM) domain, a glycine-serine (GS) rich domain, and a protein kinase domain. The numbers above the protein representation in FIG. 3a indicate the amino acids included in each identified domain.

ACVR1 Gene Structure

The intron-exon boundaries of the ACVR1 gene were obtained through GenBank, Ensembl Human Genome Server, and the University of Santa Cruz. Transcript and exon information was obtained from Ensembl (Gene ID ENSG00000115170; transcript ID ENST00000263640) which reports 11 exons for ACVR1 (exons 1 and 2 contain only 5'UTR; the protein start site is in exon 3), consistent with GenBank BC033867, full length cDNA clone. All databases for ACVR1 are consistent for the sequence information for the nine exons containing protein-coding sequences, however, additional/alternate exons containing 5'UTRs are reported through the University of Santa Cruz Genome Browser (12 exons with the protein start in exon 4) and GenBank (10 exons with the protein start in exon 2). The R206H mutation occurs in nucleotide 617 of ACVR1 cDNA (c.617G>A). [Notation follows standard nomenclature guidelines.]

Protein Structure Predictions

Structural protein homology modeling was used to determine possible biochemical consequences of the ACVR1 R206H mutation. While SWISS-MODEL analysis showed no deviation between proteins containing Arg206 or His206, both PredictProtein and CPHmodels predict a partial destabilization of the α-helix formed by ACVR1 amino acids 198-206 (FIG. 5). These models reveal that Arg202 and Arg206 are spatially orientated on the same helical face (i, i+4). Previous studies have demonstrated that the electrostatic effects of charged ion pairs can have significant helix stabilizing interactions between side chains when the spacing between residues is close to the helical repeat of 3.6 residues per turn (i.e. i, i+4). Additionally, polar side chains are often long, thus allowing their hydrophobic alkyl groups to interact favorably with nonpolar residues while keeping the polar parts free to interact with other polar groups. Side chains such as lysine and arginine can thus interact favorably with both polar and non-polar residues. Therefore, the shorter side chain of the R206H mutant is expected to cause a partial destabilization of the α-helix altering the electrostatic potential of the ACVR1 protein (FIG. 5).

Additionally the R206H mutation may impair protein-protein interactions with the GS domain. This 30 residue motif of the type I TGFβ receptor (TβR-I) kinase has two regulatory functions: (1) tight control over the basal state with FKBP12 binding to the unphosphorylated GS domain and creating a inhibitory wedge that prevents interactions with other proteins and, (2) a catalytically "open" form that binds ATP leading to protein-protein interactions with the Smad2 MH2 domains. Arginine-arginine pairs within a protein can stabilize complex formation between proteins or can stabilize regions of backbone structure through intramolecular interactions.

The effect of the R206H mutation on the predicted protein structure of the ACVR1 α-helix, residues 198-206 is shown in FIG. 5. The homology model of wild-type ACVR1 shows that the most likely conformation (lowest scoring rotamer) of the arginine 206 side chain predicts that it interacts with the α-helix backbone to stabilize the protein. Homology model of mutant R206H ACVR1 shows that the most likely conformation (lowest scoring rotamer) of the histidine 206 side chain does not interact with the α-helix backbone which is predicted to result in partial destabilization of the protein.

The Arg>His amino acid change in codon 206 appears conservative in that one positively charged amino acid is substituted for another. (In fact, in human BMPRIA and BMPRIB, codon 206 is a lysine; see FIG. 6.) However, protein modeling predicts that the shorter histidine side chain will nevertheless alter protein structure and/or protein-protein interactions. Furthermore, a non-conservative (non-positively charged) amino acid change in codon 206, may result in a lethal mutation.

Constitutively Activating Mutations in the GS Domain of Type I TGFβ Receptors

Type I TGFβ/BMP receptors contain a highly conserved 30 amino acid GS domain that is phosphorylated by ligand-bound type II receptors. Amino acid substitutions in the GS domain (T204D) have been shown to lead constitutively activating forms of TβR-I (TGF-β type I receptor). (Codon 204 in TβR-I is analogous to codon 207 in ACVR1.).

Recurrent Mutations in Human Disease

The FOP R206H ACVR1 mutation is one of the most specific codons in the human genome to be associated with a disease phenotype.

Linkage Analysis (Continued)

This approach excluded the 4q27-31 region and identified linkage of FOP to 2q23-24 in the region flanked by markers D2S1399 and D2S1238 (FIG. 2a). SNP genotyping fine-mapped the linkage region between rs1020088 (150,654,341 bp) and D2S1238 (174,505,230 bp). The multipoint lod score was 2.3 at θ=0 (see FIG. 2b).

Activin A Type I Receptor Gene (ACVR1; OMIM 102576; Also Known as Alk2 or ActRIA), a Receptor for Bone Morphogenetic Protein (BMP) is Associated with FOP No other genomic region showed consistent linkage in all five families. This genetic interval (FIG. 3a) includes the Activin A type I receptor gene (ACVR1; OMIM 102576; also known as Alk2 or ActRIA), a receptor for bone morphogenetic protein (BMP). ACVR1 is expressed in many tissues including skeletal muscle and chondrocytes. Constitutive activation of ACVR1 induces alkaline phosphatase activity in C2C12 cells, upregulates BMP4, downregulates BMP4 antagonists, expands cartilage elements, induces ectopic chondrogenesis, and stimulates joint fusions. ACVR1 is therefore a strong candidate gene for FOP which is associated with similar clinical findings and dysregulation of the BMP signaling pathway.

DNA sequence analysis of all ACVR1 protein-coding exons and splice junctions (see Table 1) revealed the presence of the identical heterozygous single nucleotide change at cDNA position 617 (c.617G>A) in all examined familial and sporadic FOP patients (FIG. 3b). We found this mutation in all affected members of seven families, including all five families used for linkage analysis (FIG. 2a). Investigation of sporadic cases of FOP patients with unambiguous clinical features revealed the presence of the identical de novo mutation in 32 of 32 cases. The examined subjects with an ACVR1 c.617G>A mutation included a patient with a previously reported, but unverifiable, mutation in the Noggin gene. In addition to direct DNA sequence analysis, the G>A nucleotide change can be verified by differential restriction endonuclease digestion (FIG. 4a).

The c.617G>A nucleotide mutation was not found in any of 159 unaffected individuals (112 unrelated controls and 47 clinically unaffected family members of patients). Unaffected family members examined included the parents of six patients with sporadic FOP. Absence of the mutation in these parents as well as in unaffected members of the linkage pedigrees (FIG. 2a) support that this mutation is fully penetrant. The ACVR1 c.617G>A nucleotide variant is not reported in SNP databases.

Sporadic cases of FOP have been reported in all racial and ethnic groups and de novo ACVR1 c.617G>A mutations were found in all groups. The pedigrees examined by linkage include several ethnicities (African-American, American-European descent, European (United Kingdom), Korean, and Native Brazilian), and haplotype analysis of markers in the linked region (FIG. 2a) demonstrates no evidence of a founder effect for the mutation.

Example 2

ASP-siRNA Specifically Inhibits the Mutant c.617A Allele

Materials and Methods
Materials

Trizol, αMEM and DMEM culture media, High Capacity RNA to cDNA reagents, and Lipofectamine RNAiMAX were obtained from Invitrogen (Carlsbad, Calif.). Human recombinant BMP4 was obtained from R&D Systems (Minneapolis, Minn., USA); stock solutions (100 ng $\mu L^{-1}$) were prepared as recommended by the manufacturer. β-glycerophosphate, ascorbic acid sodium salt, and type II collagenase were from Sigma (St Louis, Mo., USA). Sense strand of siRNAs are as shown in FIG. 8, the bold nucleotide indicates the position corresponding to nucleotide c.617. All were synthesized (Sigma) as complementary sequences (except where noted) with 3'UU overhangs. Control scrambled Alexa-fluor red 555-labeled siRNA was from Invitrogen.
SHED Cell Isolation, Culture and Treatments Exfoliated teeth were obtained from normal and FOP pediatric patients according to the Institutional Review Board-approved protocols at the University of Pennsylvania. Cells were isolated as previously reported and used up to passage 10. In brief, dental pulp was digested with 3 mg mL$^{-1}$ type II collagenase for 1 hour at 37° C., then the collagenase activity was neutralized with the addition of growth media (αMEM with 10% FCS) and filtered through a 100-mm cell strainer (BD Falcon, Franklin Lakes, N.J., USA). Cells were recovered by centrifugation (1200 rpm, 10 min) and plated in growth media containing antibiotics.

For transfection, cells were seeded at a density of $2.5 \times 10^4$ cells cm$^{-2}$, allowed to attach and transfected with siRNA duplexes (10 nM), using RNAiMax reagent (Invitrogen) according to manufacturer's instructions in serum-free containing media for 48 h. For pSmad1/5/8 detection, transfected cells were serum starved for 2 h then treated with 100 ng mL$^{-1}$ BMP4 for 1 h. For osteogenic differentiation, at 48 h following transfection, cells were cultured with osteogenic medium (αMEM, 10% FCS, 10 mM β-glycerophosphate, 50 µg mL$^{-1}$ ascorbic acid, and 10 ng mL$^{-1}$ BMP4). Media was replenished every 3 days. A Nikon eclipse TE2000-U microscope (Nikon Instruments Inc., Melville, N.Y., USA) was used for visualization of Alexa-fluor red 555-labeled control scrambled siRNA in transfected cells.
RNA Isolation, Real-Time PCR, and DNA Sequencing Cells were harvested at indicated times and RNA was isolated using TRIzol (Invitrogen), according to manufacturer's instructions. Following phase separation, 10 µg of glycogen (Roche Applied Science, Indianapolis, Ind., USA) was added to facilitate precipitation of RNA. RNA quantification was performed using a NanoDrop ND-1000 spectrophotometer (Thermo Scientific, Wilmington, Del., USA). cDNA was synthesized using High Capacity RNA-to-cDNA reagents (Applied Biosystems, Foster City, Calif., USA).

Real-time quantitative PCR reactions contained forward and reverse primers, cDNA (1:10 dilution), and Fast SYBR Green PCR Master Mix (Applied Biosystems). For wild-type ACVR1 allele detection: forward: 5'-TGGTACAAAGAA-CAGTGGCTAG-3' (SEQ ID NO: 61), mutant allele detection: forward: 5'-TGGTACAAAGAACAGTGGCTTA-3' (SEQ ID NO: 62) and common reverse primer: 5'-CCATAC-CTGCCTTTCCCGA-3' (SEQ ID NO: 63). PCR reactions for allele-specific detection was performed at extension temperature of 63° C. and primers diluted 1:4 from a 5-µM stock. Primers for detection of Runx2 forward: 5'-GGCATCAAA-CAGCCTCTTCAG-3' (SEQ ID NO: 64), reverse: 5'-GGT-GCTCGGATCCCAAAAG-3' (SEQ ID NO: 65) and for Alkaline Phosphatase forward: 5'-ACCATTCCCACGTCT-TCACATTTG-3' (SEQ ID NO: 66), reverse: 5'-AGACAT-TCTCTCGTTCACCGCC-3' (SEQ ID NO: 67). Each sample was analyzed in triplicate (Applied Biosystems 7500 Fast Real-Time PCR Systems) and target gene mRNA levels quantified from standard curves and normalized to GAPDH.

cDNA from transfected FOP SHED cells was PCR amplified (30 cycles of 94° C. 1 min, 66° C. 1 min and 72° C. 2 min) spanning the region containing nucleotide c.617. PCR products were gel-purified and the DNA sequence determined (DNA Sequencing Facility, Department of Genetics, University of Pennsylvania).
Protein Isolation and Immunoblotting Cells were harvested and lysed in two packed cell volumes of 1× lysis buffer (150 mM nacl, 100 mM EDTA, 1% NP-40, 40 mM tris, pH 7.9.10% glycerol, 0.1% SDS, and 1× protease inhibitor cocktail). Protein concentration determined by BCA Protein Assay (Pierce Biotechnology, Rockford, Ill., USA) using BSA as a standard.

Proteins were electrophoresed through 4-12% gradient SDS-polyacrylamide gels (Invitrogen) and transferred to nitrocellulose membranes. Membranes were blocked in LI-COR blocking buffer (LI-COR Biosciences, Lincoln, Nebr., USA) for 1 h and incubated with primary antibodies: 1:1,000 dilution of pSmad1/5/8 antibody (Cell Signaling Technology, Danvers, Mass., USA) and 1:4,000 dilution of β-actin antibody (Santa Cruz Biotechnology, Santa Cruz, Calif., USA) in LI-COR blocking buffer overnight at 4° C. Bound primary antibodies were detected with species matched IRDye-labeled secondary antibodies (LI-COR) diluted 1:40,000 (in LI-COR blocking buffer) for 1 h at room temperature (protected from light). Imaging and quantification of blots were performed using the Odyssey Infrared Detection System (LI-COR). Data are presented as ratios of pSmad1/5/8 intensity normalized to β-actin and results plotted relative to normal cells treated with BMP4 (set=1).

Statistics

The unpaired two-tailed Student's t-test was used to determine the significant difference between means. All relevant comparisons were significantly different at P<0.05 unless otherwise indicated. All experiments were performed at least in triplicate.

Results

Figure 7:
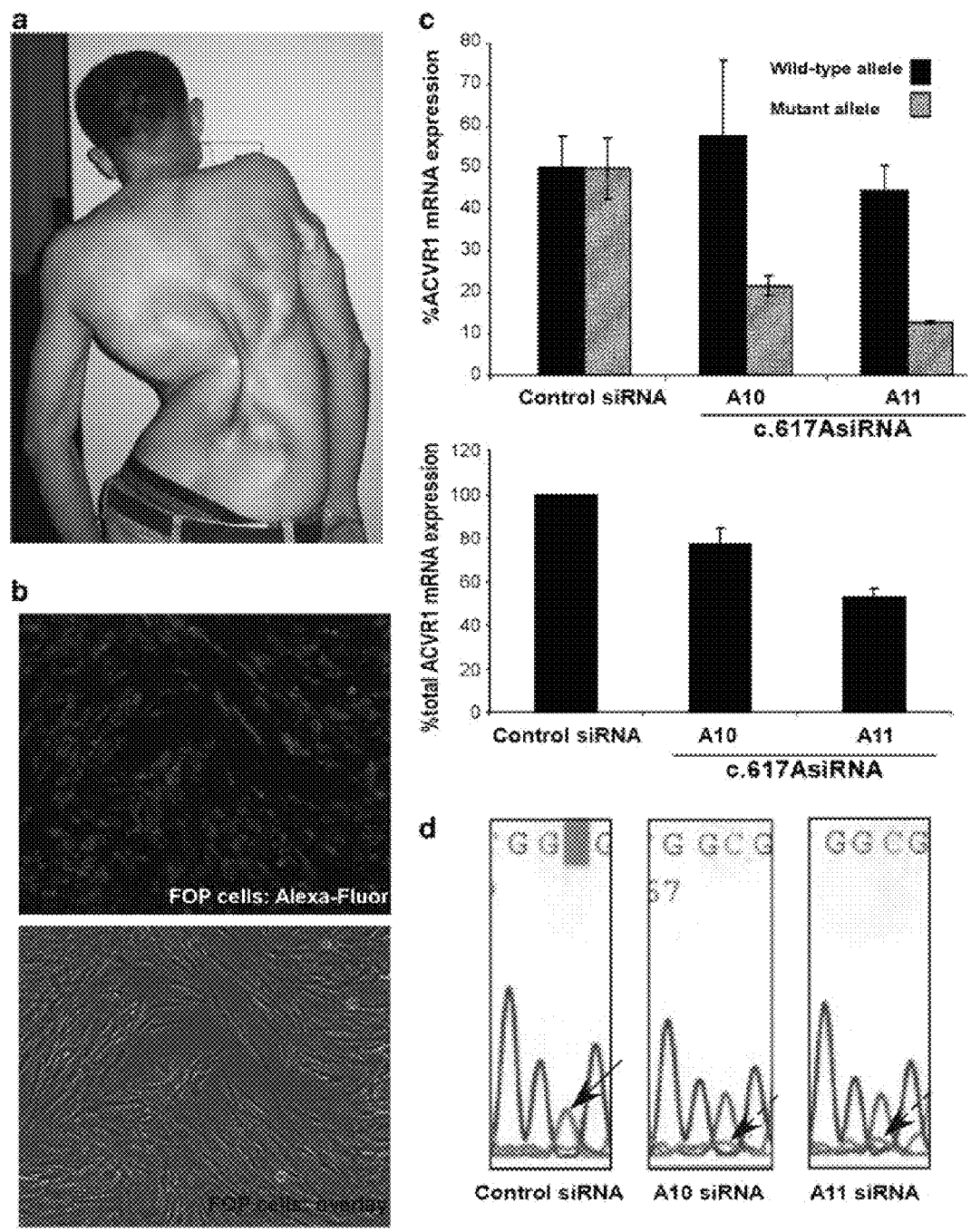
FIG. 7 shows allele specific (ASP) inhibition of the mutant c.617A allele expression in FOP SHED cells. (A) Large areas of heterotopic bone protrude from the back and right arm of an FOP patient, causing substantial deformity. (B) Top panel, FOP SHED cells that were transfected with Alexa-fluor red-labeled control siRNA for 48 h show efficient siRNA delivery (intense red fluorescence). Bottom panel, the fluorescent image is overlaid with the phase contrast image of the FOP SHED cells. (C) Top panel, FOP SHED cells were transfected with two different ASP-siRNA (A10 and A11) or control (scramble) siRNA and show selective suppression of the mutant c.617A allele expression (hatched bars); the expression of the wild-type allele is minimally affected. Bottom panel, total ACVR1 mRNA expression was reduced in siRNA-transfected cells. (D) DNA sequencing of cDNA isolated from cells transfected with control (scrambled) and mutant ASP-siRNA (A10 or A11) demonstrate specificity of targeting with reduction of the T-nucleotide peak (sequenced in reverse and corresponding to c.617A), as depicted by hatched arrows. Two overlapping peaks characteristic of heterozygous allele expression are visualized in control siRNA transfected cells (arrow)

FOP is an autosomal dominant genetic disorder of progressive heterotopic endochondral ossification that is characterized by the formation of extensive heterotopic bone that severely impairs movement and diminishes quality of life (FIG. 7a). Allele-specific RNAi (ASP-RNAi) provides an opportunity to selectively decrease signaling from the mutant allele while permitting signaling from the normal allele.

Primary dental pulp of human exfoliated deciduous teeth (SHED) cells were chosen as the model system to evaluate ASP-RNAi. These cells are patient-derived cells that endogenously express the c.617A mutant allele and are capable of differentiating into osteoblasts upon BMP stimulation. Importantly, SHED cells can be safely obtained from FOP patients without the risk of biopsy-related trauma that could induce heterotopic endochondral ossification in the patients.

To evaluate transfection efficiency, FOP SHED cells were transfected with 40 nM control scrambled Alexa-fluor red 555-labeled siRNA for 48 h. Primary FOP SHED cells are transfected efficiently with ASP-siRNA. The FOP SHED cells showed a very high level of transfection efficiency as visualized by red fluorescence staining of all cells (FIG. 7b). Furthermore, as shown in FIG. 7c, similar expression of both wild-type and mutant c.617A alleles was consistently found in FOP SHED cells demonstrating that the pathogenesis of FOP is a result of a mildly activating mutation (not dysregulated mRNA expression) of one allele. Collectively, these data demonstrate that SHED cells represent an informative model system to evaluate ASP-RNAi.

ASP-siRNA Specifically Inhibits the Mutant c.617A Allele

A series of chemically unmodified synthetic siRNA duplexes were generated containing the c.617G>A mutation tiled throughout the duplex and also including mismatches at the 5'-end of the guide strand to favor loading of the guide strand into the RNA-induced silencing complex (FIG. 8). To test whether these siRNA duplexes were capable of selectively knocking-down the mutant c.617A allele, FOP SHED cells were transfected with 10 nM of an siRNA duplex, and the level of wild-type c.617G and mutant c.617A mRNA was assessed using a qPCR assay designed to selectively detect the endogenous expression of the wild-type c.617G or the mutant c.617A allele. In FOP SHED cells that were transfected with control (scrambled) siRNA, allele-specific qPCR consistently demonstrated approximately equal expression of wild-type and mutant c.617A ACVR1 alleles (FIG. 7c, upper panel). In FOP SHED cells transfected with siRNA duplexes containing the mutant sequence, allele-specific targeting of the mutant c.617A mRNA was observed with most of the siRNA duplexes in the series (FIG. 7c, data not shown); the duplex was selected and mismatches at the 5'-end of the guide strand was also included to favor loading of the guide strand into the RNA-induced silencing complex (FIG. 8). To test whether these siRNA duplexes were capable of selectively knocking-down the mutant c.617A allele, FOP SHED cells were transfected with 10 nM of an siRNA duplex, and the level of wild-type c.617G and mutant c.617A mRNA was assessed using a qPCR assay designed to selectively detect the endogenous expression of the wild-type c.617G or the mutant c.617A allele. In FOP SHED cells that were transfected with control (scrambled) siRNA, allele-specific qPCR consistently demonstrated approximately equal expression of wild-type and mutant c.617A ACVR1 alleles (FIG. 7c, upper panel). In FOP SHED cells transfected with siRNA duplexes containing the mutant sequence, allele-specific targeting of the mutant c.617A mRNA was observed with most of the siRNA duplexes in our series (FIG. 7c, data not shown); duplexes A10 and A11 were selected for further detailed analysis. To confirm that total ACVR1 mRNA expression was decreased in ASP-siRNA transfected cells, an independent primer set amplifying both wild-type c.617G and mutant c.617A alleles indiscriminatingly demonstrated decreased levels of total ACVR1 expression following transfection of ASP-siRNA duplexes in FOP SHED cells (FIG. 7c, lower panel). Further verification of allele-specific targeting of the mutant c.617A allele was demonstrated by sequence analysis of cDNA. FOP SHED cells transfected with mutant ASP-siRNA duplexes A10 or A11 show the nearly complete absence of the mutant allele (T nucleotide peak) with predominant expression of the wild-type allele (C nucleotide peak) (FIG. 7d). These DNA sequencing data further confirm the specificity and validity of both the ASP-RNAi and the ASP-qPCR detection system. The data demonstrate that ASP-siRNA duplexes are capable of specifically and selectively suppressing the endogenous expression of the mutant c.617A allele in primary mesenchymal stem cells obtained from FOP patients.

Example 3

Phospho-Smad 1/5/8 Signaling and Osteogenic Differentiation are Restored to Control Levels in FOP SHED Cells Transfected with Mutant ASP-siRNA It was then examined whether selective suppression of the mutant c.617A allele in these cells is sufficient to reduce the elevated BMP pathway signaling from the mutant receptor to levels comparable to normal SHED cells in response to BMP ligand.

Figure 9:
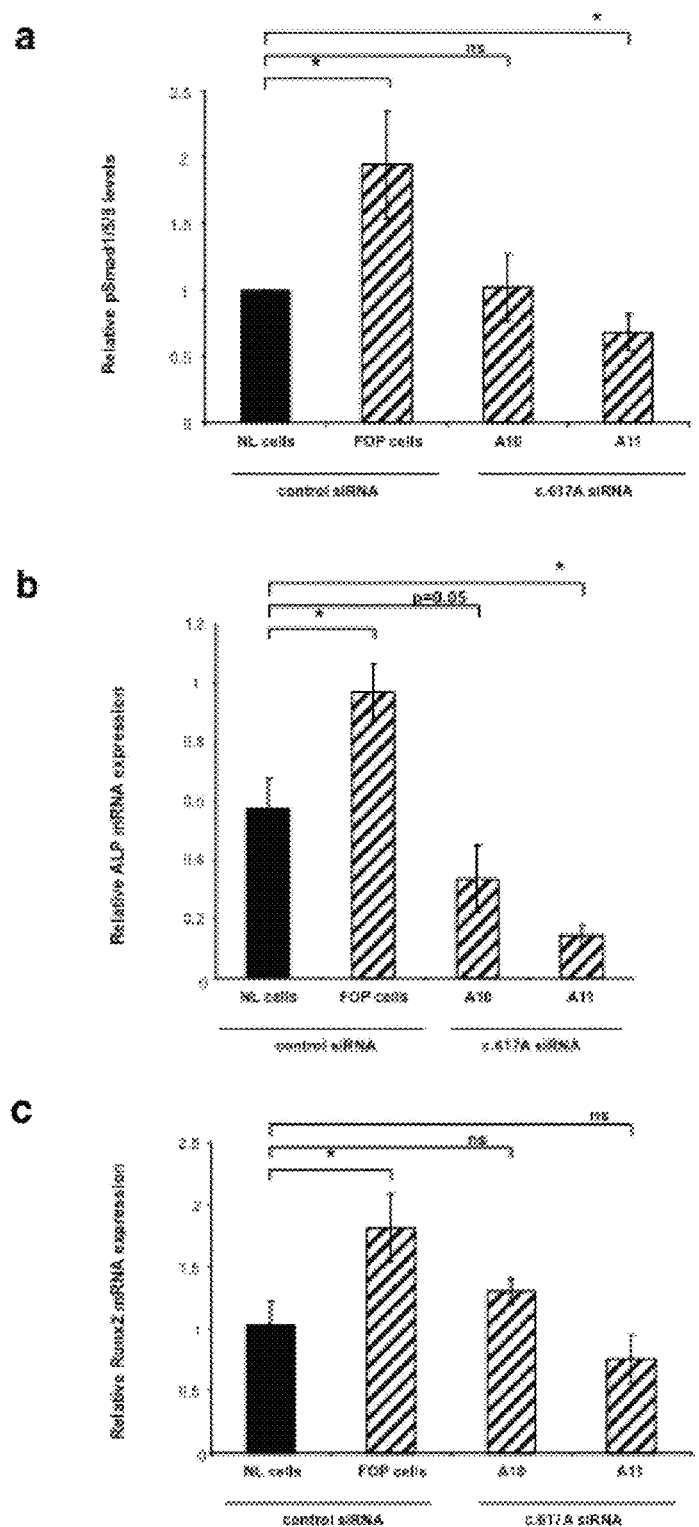
FIG. 9 shows decreased BMP signaling and osteogenic differentiation in FOP cells in response to mutant ASP-siRNA. (A) FOP SHED cells (hatched bars) were transfected with ASP-siRNA duplexes A10 and A11 and treated with BMP4 (10 ng mL$^{-1}$) for 1 hour. pSmad1/5/8 was detected by immunoblotting as an assay for BMP signaling activity. pSmad1/5/8 was quantified and compared with BMP4-treated control SHED cells (*P<0.05, compared with normal SHED cells). Relative mRNA expression in normal and FOP SHED cells (transfected with mutant ASP-siRNA duplexes A10 or A11) of the osteogenic markers alkaline phosphatase (ALP) (B) and Runx2 (C) following 3 days in osteogenic media (*P<0.05, compared with normal SHED cells).

FOP SHED cells were transfected with ASP-siRNA duplexes A10 and A11 for 48 h then treated with 10 ng mL$^{-1}$ BMP4 for 1 h. Proteins were extracted and detected for phosphorylated Smad1/5/8 (pSmad1/5/8) by immunoblotting. In response to BMP4, FOP SHED cells treated with control RNAi showed approximately two-fold higher pSmad1/5/8 compared with normal SHED cells (FIG. 9a). Following transfection with mutant ASP-siRNA duplexes, this increased pSmad1/5/8 in BMP-treated FOP cells was reduced to levels similar to normal SHED cells. The reduced or 'restored' BMP signaling levels demonstrates that allele-specific RNAi is a potential therapeutic tool to suppress the enhanced signaling driven by the expression of the mutant c.617A allele in FOP patient cells.

To determine whether mutant allele-specific knockdown would reduce the enhanced osteogenic potential of osteogenic precursor cells containing the ACVR1 R206H mutation, FOP SHED cells were cultured in the presence of mutant or wild-type ASP-siRNA duplexes under osteogenic induction conditions. Because of the nature of these chemically unmodified siRNA duplexes and, consequently, their short half-life in cell culture experiments, the effect of ASP-siRNA duplexes during short-term osteogenic differentiation of FOP SHED cells was evaluated. In response to osteogenic media, after 3 days, FOP SHED cells demonstrate significantly higher levels of early osteoblast differentiation markers, alkaline phosphatase and Runx2, compared with normal SHED cells (FIGS. 9b and 9c). Transfection of FOP SHED cells with mutant ASP-siRNA duplexes was capable of reducing the expression of alkaline phosphatase and Runx2 to levels similar to normal SHED cells. These results confirm the effectiveness of targeted suppression of the mutant c.617A allele and demonstrate that enhanced osteogenic differentiation in FOP cells is mediated through expression of the mutant c.617A allele.

Chemical modifications of siRNA duplexes, are used to enhance the stability, potency and specificity of RNAi allowing for longer-term effects both in vitro and in vivo.

In summary, chemically unmodified siRNA duplexes were used in primary FOP mesenchymal progenitor cells to specifically target suppression of the mutant c.617A allele and restored BMP signaling and osteogenic differentiation to control levels.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A method of treating Fibrodysplasia Ossificans Progressiva (FOP) in a subject, comprising the step of administering to said subject a therapeutically effective amount of a siRNA specific against a nucleic acid encoding a mutated Activin A type I receptor (ACVR1) represented by SEQ ID NO: 21 relative to a nucleic acid encoding wild-type Activin A type I receptor protein (ACVR1) as set forth in SEQ ID NO: 26, wherein said siRNA has a passenger strand selected from SEQ ID NO: 56 or SEQ ID NO: 57.

2. The method of claim 1, whereby treating comprises inhibiting, delaying onset or preventing.

3. The method of claim 1, whereby treating comprises reducing the incidence of, alleviating symptoms or both.

4. The method of claim 1, whereby the Fibrodysplasia Ossificans Progressiva (FOP) is inherited Fibrodysplasia Ossificans Progressiva (FOP).

5. The method of claim 1, whereby the Fibrodysplasia Ossificans Progressiva (FOP) is sporadic Fibrodysplasia Ossificans Progressiva (FOP).

6. A method of treating a pathology associated with heterotopic ossification in a subject, comprising the step of administering to said subject a therapeutically effective amount of a siRNA specific against a nucleic acid encoding a mutated Activin A type I receptor (ACVR1) represented by SEQ ID NO: 21 relative to a nucleic acid encoding wild-type Activin A type I receptor protein (ACVR1) as set forth in SEQ ID NO: 26, wherein said siRNA has a passenger strand selected from SEQ ID NO: 56 or SEQ ID NO: 57.

7. The method of claim 6, whereby the pathology associated with heterotopic ossification is hip replacement surgery, valvular heart disease, closed head trauma, spinal cord injuries, sports injuries, blast injuries, or a combination thereof.

8. The method of claim 7, further comprising administering to said subject a therapeutically effective amount of a BMP signal-transduction inhibitor.

9. An allele-specific siRNA, comprising a siRNA specific against a nucleic acid encoding a mutated Activin A type I receptor (ACVR1) represented by SEQ ID NO: 21 relative to a nucleic acid encoding wild-type Activin A type I receptor protein (ACVR1) as set forth in SEQ ID NO: 26 wherein said siRNA has a passenger strand selected from SEQ ID NO: 56 or SEQ ID NO: 57.

* * * * *

```
                         SEQUENCE LISTING

<160> NUMBER OF SEQ ID NOS: 67

<210> SEQ ID NO 1
<211> LENGTH: 20
<212> TYPE: DNA
<213> ORGANISM: Homo sapiens

<400> SEQUENCE: 1
ggcagtttga aggtggtatg                                              20

<210> SEQ ID NO 2
<211> LENGTH: 19
<212> TYPE: DNA
<213> ORGANISM: Homo sapiens

<400> SEQUENCE: 2
atatgaacac cacaggggg                                               19

<210> SEQ ID NO 3
<211> LENGTH: 22
<212> TYPE: DNA
<213> ORGANISM: Homo sapiens

<400> SEQUENCE: 3
tttttccccc ttcctttctc tc                                           22

<210> SEQ ID NO 4
<211> LENGTH: 22
<212> TYPE: DNA
<213> ORGANISM: Homo sapiens

<400> SEQUENCE: 4
aattccccct tttccctcca ac                                           22

<210> SEQ ID NO 5
<211> LENGTH: 21
<212> TYPE: DNA
<213> ORGANISM: Homo sapiens

<400> SEQUENCE: 5
ccagtccttc ttccttcttc c                                            21

<210> SEQ ID NO 6
<211> LENGTH: 19
<212> TYPE: DNA
<213> ORGANISM: Homo sapiens

<400> SEQUENCE: 6
tcccaagctg agtttctcc                                               19

<210> SEQ ID NO 7
<211> LENGTH: 21
```

```
<212> TYPE: DNA
<213> ORGANISM: Homo sapiens

<400> SEQUENCE: 7
gacatttact gtgtaggtcg c                                              21

<210> SEQ ID NO 8
<211> LENGTH: 22
<212> TYPE: DNA
<213> ORGANISM: Homo sapiens

<400> SEQUENCE: 8
tggggttggt ttaaaatcct tc                                             22

<210> SEQ ID NO 9
<211> LENGTH: 22
<212> TYPE: DNA
<213> ORGANISM: Homo sapiens

<400> SEQUENCE: 9
cacattataa cctgtgacac cc                                             22

<210> SEQ ID NO 10
<211> LENGTH: 19
<212> TYPE: DNA
<213> ORGANISM: Homo sapiens

<400> SEQUENCE: 10
gtattgctgc ttttggcac                                                 19

<210> SEQ ID NO 11
<211> LENGTH: 21
<212> TYPE: DNA
<213> ORGANISM: Homo sapiens

<400> SEQUENCE: 11
acccaaaaag atgtgagtca c                                              21

<210> SEQ ID NO 12
<211> LENGTH: 21
<212> TYPE: DNA
<213> ORGANISM: Homo sapiens

<400> SEQUENCE: 12
cctttctggt agacgtggaa g                                              21

<210> SEQ ID NO 13
<211> LENGTH: 20
<212> TYPE: DNA
<213> ORGANISM: Homo sapiens

<400> SEQUENCE: 13
cagggtgacc ttccttgtag                                                20

<210> SEQ ID NO 14
<211> LENGTH: 22
<212> TYPE: DNA
<213> ORGANISM: Homo sapiens

<400> SEQUENCE: 14
taagaacgtg tctccagaca cc                                             22

<210> SEQ ID NO 15
```

```
<211> LENGTH: 22
<212> TYPE: DNA
<213> ORGANISM: Homo sapiens

<400> SEQUENCE: 15
agcagatttt ccaagttcca tc                                          22

<210> SEQ ID NO 16
<211> LENGTH: 20
<212> TYPE: DNA
<213> ORGANISM: Homo sapiens

<400> SEQUENCE: 16
agagcaaagg cagacaattg                                             20

<210> SEQ ID NO 17
<211> LENGTH: 21
<212> TYPE: DNA
<213> ORGANISM: Homo sapiens

<400> SEQUENCE: 17
agagatgcaa ctcacctaac c                                           21

<210> SEQ ID NO 18
<211> LENGTH: 21
<212> TYPE: DNA
<213> ORGANISM: Homo sapiens

<400> SEQUENCE: 18
aggtagctgg atcaagagaa c                                           21

<210> SEQ ID NO 19
<211> LENGTH: 22
<212> TYPE: DNA
<213> ORGANISM: Homo sapiens

<400> SEQUENCE: 19
ataccagttg aaactcaaag gg                                          22

<210> SEQ ID NO 20
<211> LENGTH: 19
<212> TYPE: DNA
<213> ORGANISM: Homo sapiens

<400> SEQUENCE: 20
cagtccctac ctttgcaac                                              19

<210> SEQ ID NO 21
<211> LENGTH: 509
<212> TYPE: PRT
<213> ORGANISM: Homo sapiens

<400> SEQUENCE: 21
```

Met Val Asp Gly Val Met Ile Leu Pro Val Leu Ile Met Ile Ala Leu
1               5                   10                  15

Pro Ser Pro Ser Met Glu Asp Glu Lys Pro Lys Val Asn Pro Lys Leu
            20                  25                  30

Tyr Met Cys Val Cys Glu Gly Leu Ser Cys Gly Asn Glu Asp His Cys
        35                  40                  45

Glu Gly Gln Gln Cys Phe Ser Ser Leu Ser Ile Asn Asp Gly Phe His
    50                  55                  60

Val Tyr Gln Lys Gly Cys Phe Gln Val Tyr Glu Gln Gly Lys Met Thr

```
                65                  70                  75                  80
Cys Lys Thr Pro Pro Ser Pro Gly Gln Ala Val Glu Cys Cys Gln Gly
                        85                  90                  95

Asp Trp Cys Asn Arg Asn Ile Thr Ala Gln Leu Pro Thr Lys Gly Lys
                100                 105                 110

Ser Phe Pro Gly Thr Gln Asn Phe His Leu Glu Val Gly Leu Ile Ile
            115                 120                 125

Leu Ser Val Val Phe Ala Val Cys Leu Leu Ala Cys Leu Leu Gly Val
        130                 135                 140

Ala Leu Arg Lys Phe Lys Arg Arg Asn Gln Glu Arg Leu Asn Pro Arg
145                 150                 155                 160

Asp Val Glu Tyr Gly Thr Ile Glu Gly Leu Ile Thr Thr Asn Val Gly
                165                 170                 175

Asp Ser Thr Leu Ala Asp Leu Leu Asp His Ser Cys Thr Ser Gly Ser
                180                 185                 190

Gly Ser Gly Leu Pro Phe Leu Val Gln Arg Thr Val Ala His Gln Ile
            195                 200                 205

Thr Leu Leu Glu Cys Val Gly Lys Gly Arg Tyr Gly Glu Val Trp Arg
        210                 215                 220

Gly Ser Trp Gln Gly Glu Asn Val Ala Val Lys Ile Phe Ser Ser Arg
225                 230                 235                 240

Asp Glu Lys Ser Trp Phe Arg Glu Thr Glu Leu Tyr Asn Thr Val Met
                245                 250                 255

Leu Arg His Glu Asn Ile Leu Gly Phe Ile Ala Ser Asp Met Thr Ser
                260                 265                 270

Arg His Ser Ser Thr Gln Leu Trp Leu Ile Thr His Tyr His Glu Met
            275                 280                 285

Gly Ser Leu Tyr Asp Tyr Leu Gln Leu Thr Thr Leu Asp Thr Val Ser
        290                 295                 300

Cys Leu Arg Ile Val Leu Ser Ile Ala Ser Gly Leu Ala His Leu His
305                 310                 315                 320

Ile Glu Ile Phe Gly Thr Gln Gly Lys Pro Ala Ile Ala His Arg Asp
                325                 330                 335

Leu Lys Ser Lys Asn Ile Leu Val Lys Lys Asn Gly Gln Cys Cys Ile
                340                 345                 350

Ala Asp Leu Gly Leu Ala Val Met His Ser Gln Ser Thr Asn Gln Leu
            355                 360                 365

Asp Val Gly Asn Asn Pro Arg Val Gly Thr Lys Arg Tyr Met Ala Pro
        370                 375                 380

Glu Val Leu Asp Glu Thr Ile Gln Val Asp Cys Phe Asp Ser Tyr Lys
385                 390                 395                 400

Arg Val Asp Ile Trp Ala Phe Gly Leu Val Leu Trp Glu Val Ala Arg
                405                 410                 415

Arg Met Val Ser Asn Gly Ile Val Glu Asp Tyr Lys Pro Pro Phe Tyr
                420                 425                 430

Asp Val Val Pro Asn Asp Pro Ser Phe Glu Asp Met Arg Lys Val Val
            435                 440                 445

Cys Val Asp Gln Gln Arg Pro Asn Ile Pro Asn Arg Trp Phe Ser Asp
        450                 455                 460

Pro Thr Leu Thr Ser Leu Ala Lys Leu Met Lys Glu Cys Trp Tyr Gln
465                 470                 475                 480

Asn Pro Ser Ala Arg Leu Thr Ala Leu Arg Ile Lys Lys Thr Leu Thr
                485                 490                 495
```

```
Lys Ile Asp Asn Ser Leu Asp Lys Leu Lys Thr Asp Cys
            500                 505
```

```
<210> SEQ ID NO 22
<211> LENGTH: 509
<212> TYPE: PRT
<213> ORGANISM: Homo sapiens

<400> SEQUENCE: 22

Met Val Asp Gly Val Met Ile Leu Pro Val Leu Ile Met Ile Ala Leu
1               5                   10                  15

Pro Ser Pro Ser Met Glu Asp Glu Lys Pro Lys Val Asn Pro Lys Leu
            20                  25                  30

Tyr Met Cys Val Cys Glu Gly Leu Ser Cys Gly Asn Glu Asp His Cys
        35                  40                  45

Glu Gly Gln Gln Cys Phe Ser Ser Leu Ser Ile Asn Asp Gly Phe His
    50                  55                  60

Val Tyr Gln Lys Gly Cys Phe Gln Val Tyr Glu Gln Gly Lys Met Thr
65                  70                  75                  80

Cys Lys Thr Pro Pro Ser Pro Gly Gln Ala Val Glu Cys Cys Gln Gly
                85                  90                  95

Asp Trp Cys Asn Arg Asn Ile Thr Ala Gln Leu Pro Thr Lys Gly Lys
            100                 105                 110

Ser Phe Pro Gly Thr Gln Asn Phe His Leu Glu Val Gly Leu Ile Ile
        115                 120                 125

Leu Ser Val Val Phe Ala Val Cys Leu Leu Ala Cys Leu Leu Gly Val
    130                 135                 140

Ala Leu Arg Lys Phe Lys Arg Arg Asn Gln Glu Arg Leu Asn Pro Arg
145                 150                 155                 160

Asp Val Glu Tyr Gly Thr Ile Glu Gly Leu Ile Thr Thr Asn Val Gly
                165                 170                 175

Asp Ser Thr Leu Ala Asp Leu Leu Asp His Ser Cys Thr Ser Gly Ser
            180                 185                 190

Gly Ser Gly Leu Pro Phe Leu Val Gln Arg Thr Val Ala Arg Glu Ile
        195                 200                 205

Thr Leu Leu Glu Cys Val Gly Lys Gly Arg Tyr Gly Glu Val Trp Arg
    210                 215                 220

Gly Ser Trp Gln Gly Glu Asn Val Ala Val Lys Ile Phe Ser Ser Arg
225                 230                 235                 240

Asp Glu Lys Ser Trp Phe Arg Glu Thr Glu Leu Tyr Asn Thr Val Met
                245                 250                 255

Leu Arg His Glu Asn Ile Leu Gly Phe Ile Ala Ser Asp Met Thr Ser
            260                 265                 270

Arg His Ser Ser Thr Gln Leu Trp Leu Ile Thr His Tyr His Glu Met
        275                 280                 285

Gly Ser Leu Tyr Asp Tyr Leu Gln Leu Thr Thr Leu Asp Thr Val Ser
    290                 295                 300

Cys Leu Arg Ile Val Leu Ser Ile Ala Ser Gly Leu Ala His Leu His
305                 310                 315                 320

Ile Glu Ile Phe Gly Thr Gln Gly Lys Pro Ala Ile Ala His Arg Asp
                325                 330                 335

Leu Lys Ser Lys Asn Ile Leu Val Lys Lys Asn Gly Gln Cys Cys Ile
            340                 345                 350

Ala Asp Leu Gly Leu Ala Val Met His Ser Gln Ser Thr Asn Gln Leu
```

```
                355                 360                 365
Asp Val Gly Asn Asn Pro Arg Val Gly Thr Lys Arg Tyr Met Ala Pro
            370                 375                 380

Glu Val Leu Asp Glu Thr Ile Gln Val Asp Cys Phe Asp Ser Tyr Lys
385                 390                 395                 400

Arg Val Asp Ile Trp Ala Phe Gly Leu Val Leu Trp Glu Val Ala Arg
                405                 410                 415

Arg Met Val Ser Asn Gly Ile Val Glu Asp Tyr Lys Pro Pro Phe Tyr
            420                 425                 430

Asp Val Val Pro Asn Asp Pro Ser Phe Glu Asp Met Arg Lys Val Val
            435                 440                 445

Cys Val Asp Gln Gln Arg Pro Asn Ile Pro Asn Arg Trp Phe Ser Asp
            450                 455                 460

Pro Thr Leu Thr Ser Leu Ala Lys Leu Met Lys Glu Cys Trp Tyr Gln
465                 470                 475                 480

Asn Pro Ser Ala Arg Leu Thr Ala Leu Arg Ile Lys Lys Thr Leu Thr
                485                 490                 495

Lys Ile Asp Asn Ser Leu Asp Lys Leu Lys Thr Asp Cys
            500                 505

<210> SEQ ID NO 23
<211> LENGTH: 509
<212> TYPE: PRT
<213> ORGANISM: Homo sapiens

<400> SEQUENCE: 23

Met Val Asp Gly Val Met Ile Leu Pro Val Leu Ile Met Ile Ala Leu
1               5                   10                  15

Pro Ser Pro Ser Met Glu Asp Glu Lys Pro Lys Val Asn Pro Lys Leu
            20                  25                  30

Tyr Met Cys Val Cys Glu Gly Leu Ser Cys Gly Asn Glu Asp His Cys
        35                  40                  45

Glu Gly Gln Gln Cys Phe Ser Ser Leu Ser Ile Asn Asp Gly Phe His
    50                  55                  60

Val Tyr Gln Lys Gly Cys Phe Gln Val Tyr Glu Gln Gly Lys Met Thr
65                  70                  75                  80

Cys Lys Thr Pro Pro Ser Pro Gly Gln Ala Val Glu Cys Cys Gln Gly
                85                  90                  95

Asp Trp Cys Asn Arg Asn Ile Thr Ala Gln Leu Pro Thr Lys Gly Lys
            100                 105                 110

Ser Phe Pro Gly Thr Gln Asn Phe His Leu Glu Val Gly Leu Ile Ile
        115                 120                 125

Leu Ser Val Val Phe Ala Val Cys Leu Leu Ala Cys Leu Leu Gly Val
    130                 135                 140

Ala Leu Arg Lys Phe Lys Arg Arg Asn Gln Glu Arg Leu Asn Pro Arg
145                 150                 155                 160

Asp Val Glu Tyr Gly Thr Ile Glu Gly Leu Ile Thr Thr Asn Val Gly
                165                 170                 175

Asp Ser Thr Leu Ala Asp Leu Leu Asp His Ser Cys Thr Ser Gly Ser
        180                 185                 190

Gly Ser Gly Leu Pro Phe Leu Val Gln Arg Thr Val Ala Arg Gln Ile
    195                 200                 205

Thr Leu Leu Glu Cys Val Gly Lys Gly Arg Tyr Gly Glu Val Trp Arg
    210                 215                 220
```

```
Gly Ser Trp Gln Gly Glu Asn Val Ala Val Lys Ile Phe Ser Ser Arg
225                 230                 235                 240

Asp Glu Lys Ser Trp Phe Arg Glu Thr Glu Leu Tyr Asn Thr Val Met
            245                 250                 255

Leu Arg His Glu Asn Ile Leu Gly Phe Ile Ala Ser Asp Met Thr Ser
        260                 265                 270

Arg His Ser Ser Thr Gln Leu Trp Leu Ile Thr His Tyr His Glu Met
    275                 280                 285

Gly Ser Leu Tyr Asp Tyr Leu Gln Leu Thr Thr Leu Asp Thr Val Ser
290                 295                 300

Cys Leu Arg Ile Val Leu Ser Ile Ala Ser Gly Leu Ala His Leu His
305                 310                 315                 320

Ile Glu Ile Phe Gly Thr Gln Trp Lys Pro Ala Ile Ala His Arg Asp
                325                 330                 335

Leu Lys Ser Lys Asn Ile Leu Val Lys Lys Asn Gly Gln Cys Cys Ile
            340                 345                 350

Ala Asp Leu Gly Leu Ala Val Met His Ser Gln Ser Thr Asn Gln Leu
        355                 360                 365

Asp Val Gly Asn Asn Pro Arg Val Gly Thr Lys Arg Tyr Met Ala Pro
370                 375                 380

Glu Val Leu Asp Glu Thr Ile Gln Val Asp Cys Phe Asp Ser Tyr Lys
385                 390                 395                 400

Arg Val Asp Ile Trp Ala Phe Gly Leu Val Leu Trp Glu Val Ala Arg
                405                 410                 415

Arg Met Val Ser Asn Gly Ile Val Glu Asp Tyr Lys Pro Pro Phe Tyr
            420                 425                 430

Asp Val Val Pro Asn Asp Pro Ser Phe Glu Asp Met Arg Lys Val Val
        435                 440                 445

Cys Val Asp Gln Gln Arg Pro Asn Ile Pro Asn Arg Trp Phe Ser Asp
        450                 455                 460

Pro Thr Leu Thr Ser Leu Ala Lys Leu Met Lys Glu Cys Trp Tyr Gln
465                 470                 475                 480

Asn Pro Ser Ala Arg Leu Thr Ala Leu Arg Ile Lys Lys Thr Leu Thr
                485                 490                 495

Lys Ile Asp Asn Ser Leu Asp Lys Leu Lys Thr Asp Cys
            500                 505

<210> SEQ ID NO 24
<211> LENGTH: 509
<212> TYPE: PRT
<213> ORGANISM: Homo sapiens

<400> SEQUENCE: 24

Met Val Asp Gly Val Met Ile Leu Pro Val Leu Ile Met Ile Ala Leu
1               5                   10                  15

Pro Ser Pro Ser Met Glu Asp Glu Lys Pro Lys Val Asn Pro Lys Leu
            20                  25                  30

Tyr Met Cys Val Cys Glu Gly Leu Ser Cys Gly Asn Glu Asp His Cys
        35                  40                  45

Glu Gly Gln Gln Cys Phe Ser Ser Leu Ser Ile Asn Asp Gly Phe His
    50                  55                  60

Val Tyr Gln Lys Gly Cys Phe Gln Val Tyr Glu Gln Gly Lys Met Thr
65                  70                  75                  80

Cys Lys Thr Pro Pro Ser Pro Gly Gln Ala Val Glu Cys Cys Gln Gly
                85                  90                  95
```

```
Asp Trp Cys Asn Arg Asn Ile Thr Ala Gln Leu Pro Thr Lys Gly Lys
            100                 105                 110

Ser Phe Pro Gly Thr Gln Asn Phe His Leu Glu Val Gly Leu Ile Ile
        115                 120                 125

Leu Ser Val Val Phe Ala Val Cys Leu Leu Ala Cys Leu Leu Gly Val
130                 135                 140

Ala Leu Arg Lys Phe Lys Arg Arg Asn Gln Glu Arg Leu Asn Pro Arg
145                 150                 155                 160

Asp Val Glu Tyr Gly Thr Ile Glu Gly Leu Ile Thr Thr Asn Val Gly
                165                 170                 175

Asp Ser Thr Leu Ala Asp Leu Leu Asp His Ser Cys Thr Ser Gly Ser
            180                 185                 190

Gly Ser Gly Leu Pro Phe Leu Val Gln Arg Thr Val Ala Arg Gln Ile
        195                 200                 205

Thr Leu Leu Glu Cys Val Gly Lys Gly Arg Tyr Gly Glu Val Trp Arg
210                 215                 220

Gly Ser Trp Gln Gly Glu Asn Val Ala Val Lys Ile Phe Ser Ser Arg
225                 230                 235                 240

Asp Glu Lys Ser Trp Phe Arg Glu Thr Glu Leu Tyr Asn Thr Val Met
                245                 250                 255

Leu Arg His Glu Asn Ile Leu Gly Phe Ile Ala Ser Asp Met Thr Ser
            260                 265                 270

Arg His Ser Ser Thr Gln Leu Trp Leu Ile Thr His Tyr His Glu Met
        275                 280                 285

Gly Ser Leu Tyr Asp Tyr Leu Gln Leu Thr Thr Leu Asp Thr Val Ser
    290                 295                 300

Cys Leu Arg Ile Val Leu Ser Ile Ala Ser Gly Leu Ala His Leu His
305                 310                 315                 320

Ile Glu Ile Phe Gly Thr Gln Glu Lys Pro Ala Ile Ala His Arg Asp
                325                 330                 335

Leu Lys Ser Lys Asn Ile Leu Val Lys Lys Asn Gly Gln Cys Cys Ile
            340                 345                 350

Ala Asp Leu Gly Leu Ala Val Met His Ser Gln Ser Thr Asn Gln Leu
        355                 360                 365

Asp Val Gly Asn Asn Pro Arg Val Gly Thr Lys Arg Tyr Met Ala Pro
370                 375                 380

Glu Val Leu Asp Glu Thr Ile Gln Val Asp Cys Phe Asp Ser Tyr Lys
385                 390                 395                 400

Arg Val Asp Ile Trp Ala Phe Gly Leu Val Leu Trp Glu Val Ala Arg
                405                 410                 415

Arg Met Val Ser Asn Gly Ile Val Glu Asp Tyr Lys Pro Pro Phe Tyr
            420                 425                 430

Asp Val Val Pro Asn Asp Pro Ser Phe Glu Asp Met Arg Lys Val Val
        435                 440                 445

Cys Val Asp Gln Gln Arg Pro Asn Ile Pro Asn Arg Trp Phe Ser Asp
    450                 455                 460

Pro Thr Leu Thr Ser Leu Ala Lys Leu Met Lys Glu Cys Trp Tyr Gln
465                 470                 475                 480

Asn Pro Ser Ala Arg Leu Thr Ala Leu Arg Ile Lys Lys Thr Leu Thr
                485                 490                 495

Lys Ile Asp Asn Ser Leu Asp Lys Leu Lys Thr Asp Cys
            500                 505
```

<210> SEQ ID NO 25
<211> LENGTH: 509
<212> TYPE: PRT
<213> ORGANISM: Homo sapiens

<400> SEQUENCE: 25

Met Val Asp Gly Val Met Ile Leu Pro Val Leu Ile Met Ile Ala Leu
1               5                   10                  15

Pro Ser Pro Ser Met Glu Asp Glu Lys Pro Lys Val Asn Pro Lys Leu
            20                  25                  30

Tyr Met Cys Val Cys Glu Gly Leu Ser Cys Gly Asn Glu Asp His Cys
        35                  40                  45

Glu Gly Gln Gln Cys Phe Ser Ser Leu Ser Ile Asn Asp Gly Phe His
    50                  55                  60

Val Tyr Gln Lys Gly Cys Phe Gln Val Tyr Glu Gln Gly Lys Met Thr
65                  70                  75                  80

Cys Lys Thr Pro Pro Ser Pro Gly Gln Ala Val Glu Cys Cys Gln Gly
                85                  90                  95

Asp Trp Cys Asn Arg Asn Ile Thr Ala Gln Leu Pro Thr Lys Gly Lys
            100                 105                 110

Ser Phe Pro Gly Thr Gln Asn Phe His Leu Glu Val Gly Leu Ile Ile
        115                 120                 125

Leu Ser Val Val Phe Ala Val Cys Leu Leu Ala Cys Leu Leu Gly Val
    130                 135                 140

Ala Leu Arg Lys Phe Lys Arg Arg Asn Gln Glu Arg Leu Asn Pro Arg
145                 150                 155                 160

Asp Val Glu Tyr Gly Thr Ile Glu Gly Leu Ile Thr Thr Asn Val Gly
                165                 170                 175

Asp Ser Thr Leu Ala Asp Leu Leu Asp His Ser Cys Thr Ser Gly Ser
            180                 185                 190

Gly Ser Gly Leu Pro Phe Leu Val Gln Arg Thr Val Ala Arg Gln Ile
        195                 200                 205

Thr Leu Leu Glu Cys Val Gly Lys Gly Arg Tyr Gly Glu Val Trp Arg
    210                 215                 220

Gly Ser Trp Gln Gly Glu Asn Val Ala Val Lys Ile Phe Ser Ser Arg
225                 230                 235                 240

Asp Glu Lys Ser Trp Phe Arg Glu Thr Glu Leu Tyr Asn Thr Val Met
                245                 250                 255

Leu Arg His Glu Asn Ile Leu Gly Phe Ile Ala Ser Asp Met Thr Ser
            260                 265                 270

Arg His Ser Ser Thr Gln Leu Trp Leu Ile Thr His Tyr His Glu Met
        275                 280                 285

Gly Ser Leu Tyr Asp Tyr Leu Gln Leu Thr Thr Leu Asp Thr Val Ser
    290                 295                 300

Cys Leu Arg Ile Val Leu Ser Ile Ala Ser Gly Leu Ala His Leu His
305                 310                 315                 320

Ile Glu Ile Phe Gly Thr Gln Gly Lys Pro Ala Ile Ala His Arg Asp
                325                 330                 335

Leu Lys Ser Lys Asn Ile Leu Val Lys Lys Asn Gly Gln Cys Cys Ile
            340                 345                 350

Ala Asp Leu Asp Leu Ala Val Met His Ser Gln Ser Thr Asn Gln Leu
        355                 360                 365

Asp Val Gly Asn Asn Pro Arg Val Gly Thr Lys Arg Tyr Met Ala Pro
    370                 375                 380

```
Glu Val Leu Asp Glu Thr Ile Gln Val Asp Cys Phe Asp Ser Tyr Lys
385                 390                 395                 400

Arg Val Asp Ile Trp Ala Phe Gly Leu Val Leu Trp Glu Val Ala Arg
                405                 410                 415

Arg Met Val Ser Asn Gly Ile Val Glu Asp Tyr Lys Pro Pro Phe Tyr
                420                 425                 430

Asp Val Val Pro Asn Asp Pro Ser Phe Glu Asp Met Arg Lys Val Val
            435                 440                 445

Cys Val Asp Gln Gln Arg Pro Asn Ile Pro Asn Arg Trp Phe Ser Asp
450                 455                 460

Pro Thr Leu Thr Ser Leu Ala Lys Leu Met Lys Glu Cys Trp Tyr Gln
465                 470                 475                 480

Asn Pro Ser Ala Arg Leu Thr Ala Leu Arg Ile Lys Lys Thr Leu Thr
                485                 490                 495

Lys Ile Asp Asn Ser Leu Asp Lys Leu Lys Thr Asp Cys
                500                 505

<210> SEQ ID NO 26
<211> LENGTH: 509
<212> TYPE: PRT
<213> ORGANISM: Homo sapiens

<400> SEQUENCE: 26

Met Val Asp Gly Val Met Ile Leu Pro Val Leu Ile Met Ile Ala Leu
1               5                   10                  15

Pro Ser Pro Ser Met Glu Asp Glu Lys Pro Lys Val Asn Pro Lys Leu
                20                  25                  30

Tyr Met Cys Val Cys Glu Gly Leu Ser Cys Gly Asn Glu Asp His Cys
                35                  40                  45

Glu Gly Gln Gln Cys Phe Ser Ser Leu Ser Ile Asn Asp Gly Phe His
            50                  55                  60

Val Tyr Gln Lys Gly Cys Phe Gln Val Tyr Glu Gln Gly Lys Met Thr
65                  70                  75                  80

Cys Lys Thr Pro Pro Ser Pro Gly Gln Ala Val Glu Cys Cys Gln Gly
                85                  90                  95

Asp Trp Cys Asn Arg Asn Ile Thr Ala Gln Leu Pro Thr Lys Gly Lys
                100                 105                 110

Ser Phe Pro Gly Thr Gln Asn Phe His Leu Glu Val Gly Leu Ile Ile
                115                 120                 125

Leu Ser Val Val Phe Ala Val Cys Leu Leu Ala Cys Leu Leu Gly Val
            130                 135                 140

Ala Leu Arg Lys Phe Lys Arg Arg Asn Gln Glu Arg Leu Asn Pro Arg
145                 150                 155                 160

Asp Val Glu Tyr Gly Thr Ile Glu Gly Leu Ile Thr Thr Asn Val Gly
                165                 170                 175

Asp Ser Thr Leu Ala Asp Leu Leu Asp His Ser Cys Thr Ser Gly Ser
                180                 185                 190

Gly Ser Gly Leu Pro Phe Leu Val Gln Arg Thr Val Ala Arg Gln Ile
                195                 200                 205

Thr Leu Leu Glu Cys Val Gly Lys Gly Arg Tyr Gly Glu Val Trp Arg
            210                 215                 220

Gly Ser Trp Gln Gly Glu Asn Val Ala Val Lys Ile Phe Ser Ser Arg
225                 230                 235                 240

Asp Glu Lys Ser Trp Phe Arg Glu Thr Glu Leu Tyr Asn Thr Val Met
```

```
            245                 250                 255
Leu Arg His Glu Asn Ile Leu Gly Phe Ile Ala Ser Asp Met Thr Ser
            260                 265                 270

Arg His Ser Ser Thr Gln Leu Trp Leu Ile Thr His Tyr His Glu Met
        275                 280                 285

Gly Ser Leu Tyr Asp Tyr Leu Gln Leu Thr Thr Leu Asp Thr Val Ser
    290                 295                 300

Cys Leu Arg Ile Val Leu Ser Ile Ala Ser Gly Leu Ala His Leu His
305                 310                 315                 320

Ile Glu Ile Phe Gly Thr Gln Gly Lys Pro Ala Ile Ala His Arg Asp
                325                 330                 335

Leu Lys Ser Lys Asn Ile Leu Val Lys Lys Asn Gly Gln Cys Cys Ile
            340                 345                 350

Ala Asp Leu Gly Leu Ala Val Met His Ser Gln Ser Thr Asn Gln Leu
        355                 360                 365

Asp Val Gly Asn Asn Pro Arg Val Gly Thr Lys Arg Tyr Met Ala Pro
    370                 375                 380

Glu Val Leu Asp Glu Thr Ile Gln Val Asp Cys Phe Asp Ser Tyr Lys
385                 390                 395                 400

Arg Val Asp Ile Trp Ala Phe Gly Leu Val Leu Trp Glu Val Ala Arg
                405                 410                 415

Arg Met Val Ser Asn Gly Ile Val Glu Asp Tyr Lys Pro Pro Phe Tyr
            420                 425                 430

Asp Val Val Pro Asn Asp Pro Ser Phe Glu Asp Met Arg Lys Val Val
        435                 440                 445

Cys Val Asp Gln Gln Arg Pro Asn Ile Pro Asn Arg Trp Phe Ser Asp
450                 455                 460

Pro Thr Leu Thr Ser Leu Ala Lys Leu Met Lys Glu Cys Trp Tyr Gln
465                 470                 475                 480

Asn Pro Ser Ala Arg Leu Thr Ala Leu Arg Ile Lys Lys Thr Leu Thr
                485                 490                 495

Lys Ile Asp Asn Ser Leu Asp Lys Leu Lys Thr Asp Cys
            500                 505

<210> SEQ ID NO 27
<211> LENGTH: 508
<212> TYPE: PRT
<213> ORGANISM: Homo sapiens

<400> SEQUENCE: 27

Met Val Asp Gly Val Met Ile Leu Pro Val Leu Ile Met Ile Gly Leu
1               5                   10                  15

Pro Ser Pro Ser Met Glu Asp Glu Lys Pro Lys Val Asn Pro Lys Leu
            20                  25                  30

Tyr Met Cys Val Cys Glu Gly Leu Ser Cys Gly Asn Glu Asp His Cys
        35                  40                  45

Glu Gly Gln Gln Cys Phe Ser Ser Leu Ser Ile Asn Asp Gly Phe His
    50                  55                  60

Val Tyr Gln Lys Gly Cys Gln Val Tyr Glu Gln Gly Lys Met Thr Cys
65                  70                  75                  80

Lys Thr Pro Pro Ser Pro Gly Gln Ala Val Glu Cys Cys Gln Gly Asp
                85                  90                  95

Trp Cys Asn Arg Asn Ile Thr Ala Gln Leu Pro Thr Lys Gly Lys Ser
            100                 105                 110
```

Phe Pro Gly Thr Gln Asn Phe His Leu Glu Val Gly Leu Ile Ile Leu
            115                 120                 125

Ser Val Val Phe Ala Val Cys Leu Leu Ala Cys Leu Leu Gly Val Ala
130                 135                 140

Leu Arg Lys Phe Lys Arg Arg Asn Gln Glu Arg Leu Asn Pro Arg Asp
145                 150                 155                 160

Val Glu Tyr Gly Thr Ile Glu Gly Leu Ile Thr Thr Asn Val Gly Asp
                165                 170                 175

Ser Thr Leu Ala Asp Leu Leu Asp His Ser Cys Thr Ser Gly Ser Gly
            180                 185                 190

Ser Gly Leu Pro Phe Leu Val Gln Arg Thr Val Ala Arg Gln Ile Thr
        195                 200                 205

Leu Leu Glu Cys Val Gly Lys Gly Arg Tyr Gly Glu Val Trp Arg Gly
210                 215                 220

Ser Trp Gln Gly Glu Asn Val Ala Val Lys Ile Phe Ser Ser Arg Asp
225                 230                 235                 240

Glu Lys Ser Trp Phe Arg Glu Thr Glu Leu Tyr Asn Thr Val Met Leu
                245                 250                 255

Arg His Glu Asn Ile Leu Gly Phe Ile Ala Ser Asp Met Thr Ser Arg
            260                 265                 270

His Ser Ser Thr Gln Leu Trp Leu Ile Thr His Tyr His Glu Met Gly
        275                 280                 285

Ser Leu Tyr Asp Tyr Leu Gln Leu Thr Thr Leu Asp Thr Val Ser Cys
    290                 295                 300

Leu Arg Ile Val Leu Ser Ile Ala Ser Gly Leu Ala His Leu His Ile
305                 310                 315                 320

Glu Ile Phe Gly Thr Gln Gly Lys Pro Ala Ile Ala His Arg Asp Leu
                325                 330                 335

Lys Ser Lys Asn Ile Leu Val Lys Lys Asn Gly Gln Cys Cys Ile Ala
            340                 345                 350

Asp Leu Gly Leu Ala Val Met His Ser Gln Ser Thr Asn Gln Leu Asp
        355                 360                 365

Val Gly Asn Asn Pro Arg Val Gly Thr Lys Arg Tyr Met Ala Pro Glu
    370                 375                 380

Val Leu Asp Glu Thr Ile Gln Val Asp Cys Phe Asp Ser Tyr Lys Arg
385                 390                 395                 400

Val Asp Ile Trp Ala Phe Gly Leu Val Leu Trp Glu Val Ala Arg Arg
                405                 410                 415

Met Val Ser Asn Gly Ile Val Glu Asp Tyr Lys Pro Pro Phe Tyr Asp
            420                 425                 430

Val Val Pro Asn Asp Pro Ser Phe Glu Asp Met Arg Lys Val Val Cys
        435                 440                 445

Val Asp Gln Gln Arg Pro Asn Ile Pro Asn Arg Trp Phe Ser Asp Pro
    450                 455                 460

Thr Leu Thr Ser Leu Ala Lys Leu Met Lys Glu Cys Trp Tyr Gln Asn
465                 470                 475                 480

Pro Ser Ala Arg Leu Thr Ala Leu Arg Ile Lys Lys Thr Leu Thr Lys
                485                 490                 495

Ile Asp Asn Ser Leu Asp Lys Leu Lys Thr Asp Cys
            500                 505

<210> SEQ ID NO 28
<211> LENGTH: 508
<212> TYPE: PRT

<213> ORGANISM: Homo sapiens

<400> SEQUENCE: 28

```
Met Val Asp Gly Val Met Ile Leu Pro Val Leu Ile Met Ile Ala Leu
1               5                   10                  15

Pro Ser Pro Ser Met Glu Asp Glu Lys Pro Lys Val Asn Pro Lys Leu
            20                  25                  30

Tyr Met Cys Val Cys Glu Gly Leu Ser Cys Gly Asn Glu Asp His Cys
        35                  40                  45

Glu Gly Gln Gln Cys Phe Ser Ser Leu Ser Ile Asn Asp Gly Phe His
    50                  55                  60

Val Tyr Gln Lys Gly Cys Phe Gln Val Tyr Glu Gln Gly Lys Met Thr
65                  70                  75                  80

Cys Lys Thr Pro Pro Ser Pro Gly Gln Ala Val Glu Cys Cys Gln Gly
                85                  90                  95

Asp Trp Cys Asn Arg Asn Ile Thr Ala Gln Leu Pro Thr Lys Gly Lys
            100                 105                 110

Ser Phe Pro Gly Thr Gln Asn Phe His Leu Glu Val Gly Leu Ile Ile
            115                 120                 125

Leu Ser Val Val Phe Ala Val Cys Leu Leu Ala Cys Leu Leu Gly Val
130                 135                 140

Ala Leu Arg Lys Phe Lys Arg Arg Asn Gln Glu Arg Leu Asn Pro Arg
145                 150                 155                 160

Asp Val Glu Tyr Gly Thr Ile Glu Gly Leu Ile Thr Thr Asn Val Gly
                165                 170                 175

Asp Ser Thr Leu Ala Asp Leu Leu Asp His Ser Cys Thr Ser Gly Ser
            180                 185                 190

Gly Ser Gly Leu Leu Leu Val Gln Arg Thr Val Ala Arg Gln Ile Thr
            195                 200                 205

Leu Leu Glu Cys Val Gly Lys Gly Arg Tyr Gly Glu Val Trp Arg Gly
210                 215                 220

Ser Trp Gln Gly Glu Asn Val Ala Val Lys Ile Phe Ser Ser Arg Asp
225                 230                 235                 240

Glu Lys Ser Trp Phe Arg Glu Thr Glu Leu Tyr Asn Thr Val Met Leu
                245                 250                 255

Arg His Glu Asn Ile Leu Gly Phe Ile Ala Ser Asp Met Thr Ser Arg
            260                 265                 270

His Ser Ser Thr Gln Leu Trp Leu Ile Thr His Tyr His Glu Met Gly
            275                 280                 285

Ser Leu Tyr Asp Tyr Leu Gln Leu Thr Thr Leu Asp Thr Val Ser Cys
        290                 295                 300

Leu Arg Ile Val Leu Ser Ile Ala Ser Gly Leu Ala His Leu His Ile
305                 310                 315                 320

Glu Ile Phe Gly Thr Gln Gly Lys Pro Ala Ile Ala His Arg Asp Leu
                325                 330                 335

Lys Ser Lys Asn Ile Leu Val Lys Lys Asn Gly Gln Cys Cys Ile Ala
            340                 345                 350

Asp Leu Gly Leu Ala Val Met His Ser Gln Ser Thr Asn Gln Leu Asp
            355                 360                 365

Val Gly Asn Asn Pro Arg Val Gly Thr Lys Arg Tyr Met Ala Pro Glu
        370                 375                 380

Val Leu Asp Glu Thr Ile Gln Val Asp Cys Phe Asp Ser Tyr Lys Arg
385                 390                 395                 400
```

```
Val Asp Ile Trp Ala Phe Gly Leu Val Leu Trp Glu Val Ala Arg Arg
                405                 410                 415

Met Val Ser Asn Gly Ile Val Glu Asp Tyr Lys Pro Pro Phe Tyr Asp
            420                 425                 430

Val Val Pro Asn Asp Pro Ser Phe Glu Asp Met Arg Lys Val Val Cys
            435                 440                 445

Val Asp Gln Gln Arg Pro Asn Ile Pro Asn Arg Trp Phe Ser Asp Pro
450                 455                 460

Thr Leu Thr Ser Leu Ala Lys Leu Met Lys Glu Cys Trp Tyr Gln Asn
465                 470                 475                 480

Pro Ser Ala Arg Leu Thr Ala Leu Arg Ile Lys Lys Thr Leu Thr Lys
                485                 490                 495

Ile Asp Asn Ser Leu Asp Lys Leu Lys Thr Asp Cys
                500                 505

<210> SEQ ID NO 29
<211> LENGTH: 509
<212> TYPE: PRT
<213> ORGANISM: Homo sapiens

<400> SEQUENCE: 29

Met Val Asp Gly Val Met Ile Leu Pro Val Leu Ile Met Ile Ala Leu
1               5                   10                  15

Pro Ser Pro Ser Met Glu Asp Glu Lys Pro Lys Val Asn Pro Lys Leu
            20                  25                  30

Tyr Met Cys Val Cys Glu Gly Leu Ser Cys Gly Asn Glu Asp His Cys
        35                  40                  45

Glu Gly Gln Gln Cys Phe Ser Ser Leu Ser Ile Asn Asp Gly Phe His
    50                  55                  60

Val Tyr Gln Lys Gly Cys Phe Gln Val Tyr Glu Gln Gly Lys Met Thr
65                  70                  75                  80

Cys Lys Thr Pro Pro Ser Pro Gly Gln Ala Val Glu Cys Cys Gln Gly
                85                  90                  95

Asp Trp Cys Asn Arg Asn Ile Thr Ala Gln Leu Pro Thr Lys Gly Lys
            100                 105                 110

Ser Phe Pro Gly Thr Gln Asn Phe His Leu Glu Val Gly Leu Ile Ile
        115                 120                 125

Leu Ser Val Val Phe Ala Val Cys Leu Leu Ala Cys Leu Leu Gly Val
    130                 135                 140

Ala Leu Arg Lys Phe Lys Arg Arg Asn Gln Glu Arg Leu Asn Pro Arg
145                 150                 155                 160

Asp Val Glu Tyr Gly Thr Ile Glu Gly Leu Ile Thr Thr Asn Val Gly
                165                 170                 175

Asp Ser Thr Leu Ala Asp Leu Leu Asp His Ser Cys Thr Ser Gly Ser
            180                 185                 190

Gly Ser Gly Leu Pro Phe Leu Val Gln Arg Thr Val Ala Arg Glu Ile
        195                 200                 205

Thr Leu Leu Glu Cys Val Gly Lys Gly Arg Tyr Gly Glu Val Trp Arg
    210                 215                 220

Gly Ser Trp Gln Gly Glu Asn Val Ala Val Lys Ile Phe Ser Ser Arg
225                 230                 235                 240

Asp Glu Lys Ser Trp Phe Arg Glu Thr Glu Leu Tyr Asn Thr Val Met
                245                 250                 255

Leu Arg His Glu Asn Ile Leu Gly Phe Ile Ala Ser Asp Met Thr Ser
            260                 265                 270
```

```
Arg His Ser Ser Thr Gln Leu Trp Leu Ile Thr His Tyr His Glu Met
        275                 280                 285

Gly Ser Leu Tyr Asp Tyr Leu Gln Leu Thr Thr Leu Asp Thr Val Ser
    290                 295                 300

Cys Leu Arg Ile Val Leu Ser Ile Ala Ser Gly Leu Ala His Leu His
305                 310                 315                 320

Ile Glu Ile Phe Gly Thr Gln Gly Lys Pro Ala Ile Ala His Arg Asp
                325                 330                 335

Leu Lys Ser Lys Asn Ile Leu Val Lys Lys Asn Gly Gln Cys Cys Ile
            340                 345                 350

Ala Asp Leu Gly Leu Ala Val Met His Ser Gln Ser Thr Asn Gln Leu
        355                 360                 365

Asp Val Gly Asn Asn Pro Arg Val Gly Thr Lys Arg Tyr Met Ala Pro
    370                 375                 380

Glu Val Leu Asp Glu Thr Ile Gln Val Asp Cys Phe Asp Ser Tyr Lys
385                 390                 395                 400

Arg Val Asp Ile Trp Ala Phe Gly Leu Val Leu Trp Glu Val Ala Arg
                405                 410                 415

Arg Met Val Ser Asn Gly Ile Val Glu Asp Tyr Lys Pro Pro Phe Tyr
            420                 425                 430

Asp Val Val Pro Asn Asp Pro Ser Phe Glu Asp Met Arg Lys Val Val
        435                 440                 445

Cys Val Asp Gln Gln Arg Pro Asn Ile Pro Asn Arg Trp Phe Ser Asp
450                 455                 460

Pro Thr Leu Thr Ser Leu Ala Lys Leu Met Lys Glu Cys Trp Tyr Gln
465                 470                 475                 480

Asn Pro Ser Ala Arg Leu Thr Ala Leu Arg Ile Lys Lys Thr Leu Thr
                485                 490                 495

Lys Ile Asp Asn Ser Leu Asp Lys Leu Lys Thr Asp Cys
            500                 505

<210> SEQ ID NO 30
<211> LENGTH: 509
<212> TYPE: PRT
<213> ORGANISM: Homo sapiens

<400> SEQUENCE: 30

Met Val Asp Gly Val Met Ile Leu Pro Val Leu Ile Met Ile Ala Leu
1               5                   10                  15

Pro Ser Pro Ser Met Glu Asp Glu Lys Pro Lys Val Asn Pro Lys Leu
            20                  25                  30

Tyr Met Cys Val Cys Glu Gly Leu Ser Cys Gly Asn Glu Asp His Cys
        35                  40                  45

Glu Gly Gln Gln Cys Phe Ser Ser Leu Ser Ile Asn Asp Gly Phe His
    50                  55                  60

Val Tyr Gln Lys Gly Cys Phe Gln Val Tyr Glu Gln Gly Lys Met Thr
65                  70                  75                  80

Cys Lys Thr Pro Pro Ser Pro Gly Gln Ala Val Glu Cys Cys Gln Gly
                85                  90                  95

Asp Trp Cys Asn Arg Asn Ile Thr Ala Gln Leu Pro Thr Lys Gly Lys
            100                 105                 110

Ser Phe Pro Gly Thr Gln Asn Phe His Leu Glu Val Gly Leu Ile Ile
        115                 120                 125

Leu Ser Val Val Phe Ala Val Cys Leu Leu Ala Cys Leu Leu Gly Val
```

```
                130             135             140
Ala Leu Arg Lys Phe Lys Arg Arg Asn Gln Glu Arg Leu Asn Pro Arg
145                 150                 155                 160

Asp Val Glu Tyr Gly Thr Ile Glu Gly Leu Ile Thr Thr Asn Val Gly
            165                 170                 175

Asp Ser Thr Leu Ala Asp Leu Leu Asp His Ser Cys Thr Ser Gly Ser
        180                 185                 190

Gly Ser Gly Leu Pro Phe Leu Val Gln Arg Thr Val Ala Arg Gln Ile
    195                 200                 205

Thr Leu Leu Glu Cys Val Gly Lys Gly Arg Tyr Gly Glu Val Trp Arg
210                 215                 220

Gly Ser Trp Gln Gly Glu Asn Val Ala Val Lys Ile Phe Ser Ser Arg
225                 230                 235                 240

Asp Glu Lys Ser Trp Phe Arg Glu Thr Glu Leu Tyr Asn Thr Val Met
            245                 250                 255

Leu Ser His Glu Asn Ile Leu Gly Phe Ile Ala Ser Asp Met Thr Ser
        260                 265                 270

Arg His Ser Ser Thr Gln Leu Trp Leu Ile Thr His Tyr His Glu Met
    275                 280                 285

Gly Ser Leu Tyr Asp Tyr Leu Gln Leu Thr Thr Leu Asp Thr Val Ser
290                 295                 300

Cys Leu Arg Ile Val Leu Ser Ile Ala Ser Gly Leu Ala His Leu His
305                 310                 315                 320

Ile Glu Ile Phe Gly Thr Gln Gly Lys Pro Ala Ile Ala His Arg Asp
            325                 330                 335

Leu Lys Ser Lys Asn Ile Leu Val Lys Lys Asn Gly Gln Cys Cys Ile
        340                 345                 350

Ala Asp Leu Gly Leu Ala Val Met His Ser Gln Ser Thr Asn Gln Leu
    355                 360                 365

Asp Val Gly Asn Asn Pro Arg Val Gly Thr Lys Arg Tyr Met Ala Pro
370                 375                 380

Glu Val Leu Asp Glu Thr Ile Gln Val Asp Cys Phe Asp Ser Tyr Lys
385                 390                 395                 400

Arg Val Asp Ile Trp Ala Phe Gly Leu Val Leu Trp Glu Val Ala Arg
            405                 410                 415

Arg Met Val Ser Asn Gly Ile Val Glu Asp Tyr Lys Pro Pro Phe Tyr
        420                 425                 430

Asp Val Val Pro Asn Asp Pro Ser Phe Glu Asp Met Arg Lys Val Val
    435                 440                 445

Cys Val Asp Gln Gln Arg Pro Asn Ile Pro Asn Arg Trp Phe Ser Asp
450                 455                 460

Pro Thr Leu Thr Ser Leu Ala Lys Leu Met Lys Glu Cys Trp Tyr Gln
465                 470                 475                 480

Asn Pro Ser Ala Arg Leu Thr Ala Leu Arg Ile Lys Lys Thr Leu Thr
            485                 490                 495

Lys Ile Asp Asn Ser Leu Asp Lys Leu Lys Thr Asp Cys
        500                 505
```

<210> SEQ ID NO 31
<211> LENGTH: 509
<212> TYPE: PRT
<213> ORGANISM: Homo sapiens

<400> SEQUENCE: 31

-continued

```
Met Val Asp Gly Val Met Ile Leu Pro Val Leu Ile Met Ile Ala Leu
1               5                   10                  15

Pro Ser Pro Ser Met Glu Asp Glu Lys Pro Lys Val Asn Pro Lys Leu
            20                  25                  30

Tyr Met Cys Val Cys Glu Gly Leu Ser Cys Gly Asn Glu Asp His Cys
        35                  40                  45

Glu Gly Gln Gln Cys Phe Ser Ser Leu Ser Ile Asn Asp Gly Phe His
    50                  55                  60

Val Tyr Gln Lys Gly Cys Phe Gln Val Tyr Glu Gln Gly Lys Met Thr
65                  70                  75                  80

Cys Lys Thr Pro Pro Ser Pro Gly Gln Ala Val Glu Cys Cys Gln Gly
                85                  90                  95

Asp Trp Cys Asn Arg Asn Ile Thr Ala Gln Leu Pro Thr Lys Gly Lys
            100                 105                 110

Ser Phe Pro Gly Thr Gln Asn Phe His Leu Glu Val Gly Leu Ile Ile
            115                 120                 125

Leu Ser Val Val Phe Ala Val Cys Leu Leu Ala Cys Leu Leu Gly Val
    130                 135                 140

Ala Leu Arg Lys Phe Lys Arg Arg Asn Gln Glu Arg Leu Asn Pro Arg
145                 150                 155                 160

Asp Val Glu Tyr Gly Thr Ile Glu Gly Leu Ile Thr Thr Asn Val Gly
                165                 170                 175

Asp Ser Thr Leu Ala Asp Leu Leu Asp His Ser Cys Thr Ser Gly Ser
            180                 185                 190

Gly Ser Gly Leu Pro Phe Leu Val Gln Arg Thr Val Ala Arg Gln Ile
            195                 200                 205

Thr Leu Leu Glu Cys Val Gly Lys Gly Arg Tyr Gly Glu Val Trp Arg
    210                 215                 220

Gly Ser Trp Gln Gly Glu Asn Val Ala Val Lys Ile Phe Ser Ser Arg
225                 230                 235                 240

Asp Glu Lys Ser Trp Phe Arg Glu Thr Glu Leu Tyr Asn Thr Val Met
                245                 250                 255

Leu Arg His Glu Asn Ile Leu Gly Phe Ile Ala Ser Asp Met Thr Ser
            260                 265                 270

Arg His Ser Ser Thr Gln Leu Trp Leu Ile Thr His Tyr His Glu Met
        275                 280                 285

Gly Ser Leu Tyr Asp Tyr Leu Gln Leu Thr Thr Leu Asp Thr Val Ser
    290                 295                 300

Cys Leu Arg Ile Val Leu Ser Ile Ala Ser Gly Leu Ala His Leu His
305                 310                 315                 320

Ile Glu Ile Phe Gly Thr Gln Arg Lys Pro Ala Ile Ala His Arg Asp
                325                 330                 335

Leu Lys Ser Lys Asn Ile Leu Val Lys Lys Asn Gly Gln Cys Cys Ile
            340                 345                 350

Ala Asp Leu Gly Leu Ala Val Met His Ser Gln Ser Thr Asn Gln Leu
        355                 360                 365

Asp Val Gly Asn Asn Pro Arg Val Gly Thr Lys Arg Tyr Met Ala Pro
    370                 375                 380

Glu Val Leu Asp Glu Thr Ile Gln Val Asp Cys Phe Asp Ser Tyr Lys
385                 390                 395                 400

Arg Val Asp Ile Trp Ala Phe Gly Leu Val Leu Trp Glu Val Ala Arg
                405                 410                 415

Arg Met Val Ser Asn Gly Ile Val Glu Asp Tyr Lys Pro Pro Phe Tyr
```

```
                420                 425                 430
Asp Val Val Pro Asn Asp Pro Ser Phe Glu Asp Met Arg Lys Val Val
            435                 440                 445

Cys Val Asp Gln Gln Arg Pro Asn Ile Pro Asn Arg Trp Phe Ser Asp
        450                 455                 460

Pro Thr Leu Thr Ser Leu Ala Lys Leu Met Lys Glu Cys Trp Tyr Gln
465                 470                 475                 480

Asn Pro Ser Ala Arg Leu Thr Ala Leu Arg Ile Lys Lys Thr Leu Thr
                485                 490                 495

Lys Ile Asp Asn Ser Leu Asp Lys Leu Lys Thr Asp Cys
            500                 505

<210> SEQ ID NO 32
<211> LENGTH: 509
<212> TYPE: PRT
<213> ORGANISM: Homo sapiens

<400> SEQUENCE: 32

Met Val Asp Gly Val Met Ile Leu Pro Val Leu Ile Met Ile Ala Leu
1               5                   10                  15

Pro Ser Pro Ser Met Glu Asp Glu Lys Pro Lys Val Asn Pro Lys Leu
            20                  25                  30

Tyr Met Cys Val Cys Glu Gly Leu Ser Cys Gly Asn Glu Asp His Cys
        35                  40                  45

Glu Gly Gln Gln Cys Phe Ser Ser Leu Ser Ile Asn Asp Gly Phe His
    50                  55                  60

Val Tyr Gln Lys Gly Cys Phe Gln Val Tyr Glu Gln Gly Lys Met Thr
65                  70                  75                  80

Cys Lys Thr Pro Pro Ser Pro Gly Gln Ala Val Glu Cys Cys Gln Gly
                85                  90                  95

Asp Trp Cys Asn Arg Asn Ile Thr Ala Gln Leu Pro Thr Lys Gly Lys
            100                 105                 110

Ser Phe Pro Gly Thr Gln Asn Phe His Leu Glu Val Gly Leu Ile Ile
        115                 120                 125

Leu Ser Val Val Phe Ala Val Cys Leu Leu Ala Cys Leu Leu Gly Val
    130                 135                 140

Ala Leu Arg Lys Phe Lys Arg Arg Asn Gln Glu Arg Leu Asn Pro Arg
145                 150                 155                 160

Asp Val Glu Tyr Gly Thr Ile Glu Gly Leu Ile Thr Thr Asn Val Gly
                165                 170                 175

Asp Ser Thr Leu Ala Asp Leu Leu Asp His Ser Cys Thr Ser Gly Ser
            180                 185                 190

Gly Ser Gly Leu Pro Phe Leu Val Gln Arg Thr Val Ala Arg Gln Ile
        195                 200                 205

Thr Leu Leu Glu Cys Val Gly Lys Gly Arg Tyr Gly Glu Val Trp Arg
    210                 215                 220

Gly Ser Trp Gln Gly Glu Asn Val Ala Val Lys Ile Phe Ser Ser Arg
225                 230                 235                 240

Asp Glu Lys Ser Trp Phe Arg Glu Thr Glu Leu Tyr Asn Thr Val Met
                245                 250                 255

Leu Arg His Glu Asn Ile Leu Gly Phe Ile Ala Ser Asp Met Thr Ser
            260                 265                 270

Arg His Ser Ser Thr Gln Leu Trp Leu Ile Thr His Tyr His Glu Met
        275                 280                 285
```

Gly Ser Leu Tyr Asp Tyr Leu Gln Leu Thr Thr Leu Asp Thr Val Ser
            290                 295                 300
Cys Leu Arg Ile Val Leu Ser Ile Ala Ser Gly Leu Ala His Leu His
305                 310                 315                 320
Ile Glu Ile Phe Gly Thr Gln Gly Lys Pro Ala Ile Ala His Arg Asp
                325                 330                 335
Leu Lys Ser Lys Asn Ile Leu Val Lys Lys Asn Gly Gln Cys Cys Ile
            340                 345                 350
Ala Asp Leu Gly Leu Ala Val Met His Ser Gln Ser Thr Asn Gln Leu
        355                 360                 365
Asp Val Gly Asn Asn Pro Pro Val Gly Thr Lys Arg Tyr Met Ala Pro
    370                 375                 380
Glu Val Leu Asp Glu Thr Ile Gln Val Asp Cys Phe Asp Ser Tyr Lys
385                 390                 395                 400
Arg Val Asp Ile Trp Ala Phe Gly Leu Val Leu Trp Glu Val Ala Arg
                405                 410                 415
Arg Met Val Ser Asn Gly Ile Val Glu Asp Tyr Lys Pro Pro Phe Tyr
            420                 425                 430
Asp Val Val Pro Asn Asp Pro Ser Phe Glu Asp Met Arg Lys Val Val
        435                 440                 445
Cys Val Asp Gln Gln Arg Pro Asn Ile Pro Asn Arg Trp Phe Ser Asp
    450                 455                 460
Pro Thr Leu Thr Ser Leu Ala Lys Leu Met Lys Glu Cys Trp Tyr Gln
465                 470                 475                 480
Asn Pro Ser Ala Arg Leu Thr Ala Leu Arg Ile Lys Lys Thr Leu Thr
                485                 490                 495
Lys Ile Asp Asn Ser Leu Asp Lys Leu Lys Thr Asp Cys
            500                 505

<210> SEQ ID NO 33
<211> LENGTH: 7
<212> TYPE: PRT
<213> ORGANISM: Homo sapiens
<220> FEATURE:
<221> NAME/KEY: Variant
<222> LOCATION: (4)..(4)
<223> OTHER INFORMATION: R or H

<400> SEQUENCE: 33

Thr Val Ala Xaa Gln Ile Thr
1               5

<210> SEQ ID NO 34
<211> LENGTH: 21
<212> TYPE: DNA
<213> ORGANISM: Homo sapiens
<220> FEATURE:
<221> NAME/KEY: Variant
<222> LOCATION: (11)..(11)
<223> OTHER INFORMATION: G or A

<400> SEQUENCE: 34
acagtggctc rccagattac a                                                 21

<210> SEQ ID NO 35
<211> LENGTH: 7
<212> TYPE: PRT
<213> ORGANISM: Homo sapiens

<400> SEQUENCE: 35

```
Thr Val Ala Arg Gln Ile Thr
1               5
```

<210> SEQ ID NO 36
<211> LENGTH: 21
<212> TYPE: DNA
<213> ORGANISM: Homo sapiens

<400> SEQUENCE: 36

```
acagtggctc gccagattac a                                             21
```

<210> SEQ ID NO 37
<211> LENGTH: 31
<212> TYPE: PRT
<213> ORGANISM: Homo sapiens

<400> SEQUENCE: 37

```
Ser Thr Leu Ala Asp Leu Leu Asp His Ser Cys Thr Ser Gly Ser Gly
1               5                   10                  15

Ser Gly Leu Pro Phe Leu Val Gln Arg Thr Val Ala His Gln Ile
            20                  25                  30
```

<210> SEQ ID NO 38
<211> LENGTH: 31
<212> TYPE: PRT
<213> ORGANISM: Homo sapiens

<400> SEQUENCE: 38

```
Ser Thr Leu Ala Asp Leu Leu Asp His Ser Cys Thr Ser Gly Ser Gly
1               5                   10                  15

Ser Gly Leu Pro Phe Leu Val Gln Arg Thr Val Ala Arg Gln Ile
            20                  25                  30
```

<210> SEQ ID NO 39
<211> LENGTH: 31
<212> TYPE: PRT
<213> ORGANISM: Mus musculus

<400> SEQUENCE: 39

```
Ser Thr Leu Ala Glu Leu Leu Asp His Ser Cys Thr Ser Gly Ser Gly
1               5                   10                  15

Ser Gly Leu Pro Phe Leu Val Gln Arg Thr Val Ala Arg Gln Ile
            20                  25                  30
```

<210> SEQ ID NO 40
<211> LENGTH: 31
<212> TYPE: PRT
<213> ORGANISM: Xenopus laevis

<400> SEQUENCE: 40

```
Ser Thr Leu Ala Glu Met Leu Asp His Ser Cys Thr Ser Gly Ser Gly
1               5                   10                  15

Ser Gly Leu Pro Phe Leu Val Gln Arg Thr Val Ala Arg Gln Ile
            20                  25                  30
```

<210> SEQ ID NO 41
<211> LENGTH: 31
<212> TYPE: PRT
<213> ORGANISM: Danio rerio

<400> SEQUENCE: 41

```
Ser Thr Leu Ala Asp Leu Met Asp His Ser Cys Thr Ser Gly Ser Gly
1               5                   10                  15
```

-continued

Ser Gly Leu Pro Phe Leu Val Gln Arg Thr Val Ala His Gln Ile
            20                  25                  30

<210> SEQ ID NO 42
<211> LENGTH: 35
<212> TYPE: PRT
<213> ORGANISM: Homo sapiens

<400> SEQUENCE: 42

Ser Thr Leu Ala Asp Leu Leu Asp His Ser Cys Thr Ser Gly Ser Gly
1               5                   10                  15

Ser Gly Leu Pro Phe Leu Val Gln Arg Thr Val Ala His Gln Ile Thr
            20                  25                  30

Leu Leu Glu
        35

<210> SEQ ID NO 43
<211> LENGTH: 35
<212> TYPE: PRT
<213> ORGANISM: Homo sapiens

<400> SEQUENCE: 43

Ser Thr Leu Ala Asp Leu Leu Asp His Ser Cys Thr Ser Gly Ser Gly
1               5                   10                  15

Ser Gly Leu Pro Phe Leu Val Gln Arg Thr Val Ala Arg Gln Ile Thr
            20                  25                  30

Leu Leu Glu
        35

<210> SEQ ID NO 44
<211> LENGTH: 35
<212> TYPE: PRT
<213> ORGANISM: Homo sapiens

<400> SEQUENCE: 44

Lys Thr Leu Gln Asp Leu Val Tyr Asp Leu Ser Thr Ser Gly Ser Gly
1               5                   10                  15

Ser Gly Leu Pro Leu Phe Val Gln Arg Thr Val Ala Arg Thr Ile Val
            20                  25                  30

Leu Gln Glu
        35

<210> SEQ ID NO 45
<211> LENGTH: 35
<212> TYPE: PRT
<213> ORGANISM: Homo sapiens

<400> SEQUENCE: 45

Lys Thr Leu Lys Asp Leu Ile Tyr Asp Val Thr Ala Ser Gly Ser Gly
1               5                   10                  15

Ser Gly Leu Pro Leu Leu Val Gln Arg Thr Ile Ala Arg Thr Ile Val
            20                  25                  30

Leu Gln Glu
        35

<210> SEQ ID NO 46
<211> LENGTH: 35
<212> TYPE: PRT
<213> ORGANISM: Homo sapiens

<400> SEQUENCE: 46

Thr Met Leu Gly Asp Leu Leu Asp Ser Asp Cys Thr Thr Gly Ser Gly
1               5                   10                  15

Ser Gly Leu Pro Phe Leu Val Gln Arg Thr Val Ala Arg Gln Val Ala
            20                  25                  30

Leu Val Glu
        35

<210> SEQ ID NO 47
<211> LENGTH: 35
<212> TYPE: PRT
<213> ORGANISM: Homo sapiens

<400> SEQUENCE: 47

Glu Ser Leu Lys Asp Leu Ile Asp Gln Ser Gln Ser Ser Gly Ser Gly
1               5                   10                  15

Ser Gly Leu Pro Leu Leu Val Gln Arg Thr Ile Ala Lys Gln Ile Gln
            20                  25                  30

Met Val Arg
        35

<210> SEQ ID NO 48
<211> LENGTH: 35
<212> TYPE: PRT
<213> ORGANISM: Homo sapiens

<400> SEQUENCE: 48

Glu Ser Leu Arg Asp Leu Ile Glu Gln Ser Gln Ser Ser Gly Ser Gly
1               5                   10                  15

Ser Gly Leu Pro Leu Leu Val Gln Arg Thr Ile Ala Lys Gln Ile Gln
            20                  25                  30

Met Val Lys
        35

<210> SEQ ID NO 49
<211> LENGTH: 19
<212> TYPE: PRT
<213> ORGANISM: Homo sapiens

<400> SEQUENCE: 49

Thr Gly Leu Pro Leu Leu Val Gln Arg Thr Ile Ala Arg Thr Ile Val
1               5                   10                  15

Leu Gln Glu

<210> SEQ ID NO 50
<211> LENGTH: 1530
<212> TYPE: DNA
<213> ORGANISM: Homo sapiens

<400> SEQUENCE: 50
atggtagatg gagtgatgat tcttcctgtg cttatcatga ttgctctccc ctcccctagt     60
atggaagatg agaagcccaa ggtcaacccc aaactctaca tgtgtgtgtg tgaaggtctc    120
tcctgcggta atgaggacca ctgtgaaggc cagcagtgct tttcctcact gagcatcaac    180
gatggcttcc acgtctacca gaaaggctgc ttccaggttt atgagcaggg aaagatgacc    240
tgtaagaccc cgccgtcccc tggccaagct gtggagtgct gccaagggga ctggtgtaac    300
aggaacatca cggcccagct gcccactaaa ggaaaatcct tccctggaac acagaatttc    360
cacttggagg ttggcctcat tattctctct gtagtgttcg cagtatgtct tttagcctgc    420

```
ctgctgggag ttgctctccg aaaatttaaa aggcgcaacc aagaacgcct caatccccga    480
gacgtggagt atggcactat cgaagggctc atcaccacca atgttggaga cagcacttta    540
gcagatttat tggatcattc gtgtacatca ggaagtggct ctggtcttcc tttctggta    600 caaagaacag tggctcgcca gattacactg ttggagtgtg tcgggaaagg caggtatggt    660
gaggtgtgga ggggcagctg gcaaggggaa aatgttgccg tgaagatctt ctcctcccgt    720
gatgagaagt catggttcag ggaaacggaa ttgtacaaca ctgtgatgct gaggcatgaa    780
aatatcttag gtttcattgc ttcagacatg acatcaagac actccagtac ccagctgtgg    840
ttaattacac attatcatga atgggatcg ttgtacgact atcttcagct tactactctg    900
gatacagtta gctgccttcg aatagtgctg tccatagcta gtggtcttgc acatttgcac    960
atagagatat ttgggaccca agggaaacca gccattgccc atcgagattt aaagagcaaa   1020
aatattctgg ttaagaagaa tggacagtgt tgcatagcag atttgggcct ggcagtcatg   1080
cattcccaga gcaccaatca gcttgatgtg gggaacaatc cccgtgtggg caccaagcgc   1140
tacatggccc ccgaagttct agatgaaacc atccaggtgg attgtttcga ttcttataaa   1200
agggtcgata tttgggcctt tggacttgtt ttgtgggaag tggccaggcg gatggtgagc   1260
aatggtatag tggaggatta caagccaccg ttctacgatg tggttcccaa tgacccaagt   1320
tttgaagata tgaggaaggt agtctgtgtg gatcaacaaa ggccaaacat acccaacaga   1380
tggttctcag acccgacatt aacctctctg gccaagctaa tgaaagaatg ctggtatcaa   1440
aatccatccg caagactcac agcactgcgt atcaaaaaga ctttgaccaa aattgataat   1500
tccctcgaca aattgaaaac tgactgttga                                    1530

<210> SEQ ID NO 51
<211> LENGTH: 32
<212> TYPE: DNA
<213> ORGANISM: Homo sapiens

<400> SEQUENCE: 51
aacagtggct cgccagatta cactgttgga gt                                   32

<210> SEQ ID NO 52
<211> LENGTH: 32
<212> TYPE: DNA
<213> ORGANISM: Homo sapiens

<400> SEQUENCE: 52
aacagtggct caccagatta cactgttgga gt                                   32

<210> SEQ ID NO 53
<211> LENGTH: 21
<212> TYPE: RNA
<213> ORGANISM: Homo sapiens

<400> SEQUENCE: 53
uggcucacca gauuacacuu u                                               21

<210> SEQ ID NO 54
<211> LENGTH: 21
<212> TYPE: RNA
<213> ORGANISM: Homo sapiens

<400> SEQUENCE: 54
guggcucacc agauuacacu u                                               21
```

```
<210> SEQ ID NO 55
<211> LENGTH: 21
<212> TYPE: RNA
<213> ORGANISM: Homo sapiens

<400> SEQUENCE: 55
aguggcucac cagauuacau u                                              21

<210> SEQ ID NO 56
<211> LENGTH: 21
<212> TYPE: RNA
<213> ORGANISM: Homo sapiens

<400> SEQUENCE: 56
caguggcuca ccagauuacu u                                              21

<210> SEQ ID NO 57
<211> LENGTH: 21
<212> TYPE: RNA
<213> ORGANISM: Homo sapiens

<400> SEQUENCE: 57
acaguggcuc accagauuau u                                              21

<210> SEQ ID NO 58
<211> LENGTH: 21
<212> TYPE: RNA
<213> ORGANISM: Homo sapiens

<400> SEQUENCE: 58
aacaguggcu caccagauuu u                                              21

<210> SEQ ID NO 59
<211> LENGTH: 21
<212> TYPE: RNA
<213> ORGANISM: Homo sapiens

<400> SEQUENCE: 59
caguggcuca ccagauuaau u                                              21

<210> SEQ ID NO 60
<211> LENGTH: 21
<212> TYPE: RNA
<213> ORGANISM: Homo sapiens

<400> SEQUENCE: 60
caguggcuca ccagauuagu u                                              21

<210> SEQ ID NO 61
<211> LENGTH: 22
<212> TYPE: DNA
<213> ORGANISM: Homo sapiens

<400> SEQUENCE: 61
tggtacaaag aacagtggct ag                                             22

<210> SEQ ID NO 62
<211> LENGTH: 22
<212> TYPE: DNA
<213> ORGANISM: Homo sapiens

<400> SEQUENCE: 62
tggtacaaag aacagtggct ta                                             22
```

```
<210> SEQ ID NO 63
<211> LENGTH: 19
<212> TYPE: DNA
<213> ORGANISM: Homo sapiens

<400> SEQUENCE: 63
ccatacctgc ctttcccga                                           19

<210> SEQ ID NO 64
<211> LENGTH: 21
<212> TYPE: DNA
<213> ORGANISM: Homo sapiens

<400> SEQUENCE: 64
ggcatcaaac agcctcttca g                                        21

<210> SEQ ID NO 65
<211> LENGTH: 19
<212> TYPE: DNA
<213> ORGANISM: Homo sapiens

<400> SEQUENCE: 65
ggtgctcgga tcccaaaag                                           19

<210> SEQ ID NO 66
<211> LENGTH: 24
<212> TYPE: DNA
<213> ORGANISM: Homo sapiens

<400> SEQUENCE: 66
accattccca cgtcttcaca tttg                                     24

<210> SEQ ID NO 67
<211> LENGTH: 22
<212> TYPE: DNA
<213> ORGANISM: Homo sapiens

<400> SEQUENCE: 67
agacattctc tcgttcaccg cc                                       22
```